United States Patent
Bovard et al.

(10) Patent No.: US 12,012,584 B2
(45) Date of Patent: Jun. 18, 2024

(54) CELL CULTURE PLATE, DEVICES AND METHODS FOR IN VITRO EXPOSURE

(71) Applicant: PHILIP MORRIS PRODUCTS S.A., Neuchatel (CH)

(72) Inventors: David Bovard, Zug (CH); Julia Hoeng, Corcelles (CH); Shoaib Majeed, Neuchatel (CH); Antonin Sandoz, Geneva (CH)

(73) Assignee: Philip Morris Products S.A., Neuchatel (CH)

( * ) Notice: Subject to any disclaimer, the term of this patent is extended or adjusted under 35 U.S.C. 154(b) by 325 days.

(21) Appl. No.: 16/640,401

(22) PCT Filed: Aug. 30, 2018

(86) PCT No.: PCT/EP2018/073409
§ 371 (c)(1),
(2) Date: Feb. 20, 2020

(87) PCT Pub. No.: WO2019/043130
PCT Pub. Date: Mar. 7, 2019

(65) Prior Publication Data
US 2020/0339938 A1    Oct. 29, 2020

(30) Foreign Application Priority Data

Aug. 31, 2017  (EP) ..................... 17188871
Dec. 20, 2017  (EP) ..................... 17208969

(51) Int. Cl.
*C12M 1/00*    (2006.01)
*C12M 1/12*    (2006.01)
(Continued)

(52) U.S. Cl.
CPC ............ *C12M 41/14* (2013.01); *C12M 23/12* (2013.01); *C12M 23/20* (2013.01); *C12M 23/26* (2013.01);
(Continued)

(58) Field of Classification Search
CPC ...... C12M 41/14; C12M 23/12; C12M 23/20; C12M 23/26; C12M 23/38; C12M 23/40;
(Continued)

(56) References Cited

U.S. PATENT DOCUMENTS

| 5,863,792 A   | 1/1999 | Barker |
| 6,197,575 B1* | 3/2001 | Griffith .............. G01N 33/5008 435/395 |

(Continued)

FOREIGN PATENT DOCUMENTS

| DE | 69808352    | 6/2003 |
| DE | 202014105173 | 2/2015 |

(Continued)

OTHER PUBLICATIONS

Bahl, Vasundhra et al., "Thirdhand Smoke: Chemical Dynamics, Cytotoxicity, and Genotoxicity in Outdoor and Indoor Environments," *Toxicology in Vitro*, 32 (2016), 220-231.

(Continued)

*Primary Examiner* — William H. Beisner
*Assistant Examiner* — Danielle B Henkel
(74) *Attorney, Agent, or Firm* — Mueting Raasch Group

(57) ABSTRACT

There is disclosed a cell culture plate comprising at least two sequentially arranged wells and a channel adapted for fluid communication between the wells, wherein the channel is connected or coupled to a first pump via openings at each end of the channel, and wherein said first pump is operable to circulate fluid between the at least two wells. Devices and (Continued)

systems incorporating the cell culture plate and methods and uses employing same are also disclosed.

22 Claims, 23 Drawing Sheets

(51) Int. Cl.
*C12M 1/32* (2006.01)
*C12M 1/34* (2006.01)
*C12M 1/36* (2006.01)
*C12M 1/42* (2006.01)

(52) U.S. Cl.
CPC ............ *C12M 23/38* (2013.01); *C12M 23/40* (2013.01); *C12M 25/04* (2013.01); *C12M 29/12* (2013.01); *C12M 35/08* (2013.01); *C12M 41/46* (2013.01); *C12M 41/48* (2013.01)

(58) Field of Classification Search
CPC ...... C12M 25/04; C12M 29/12; C12M 35/08; C12M 41/46; C12M 41/48
See application file for complete search history.

(56) References Cited

U.S. PATENT DOCUMENTS

| | | | | |
|---|---|---|---|---|
| 6,695,765 | B1 * | 2/2004 | Beebe | A61B 17/435 600/33 |
| 7,326,385 | B2 | 2/2008 | Everett | |
| 9,964,556 | B2 | 5/2018 | Gebetsroither | |
| 2007/0048727 | A1 * | 3/2007 | Shuler | C12M 21/08 435/284.1 |
| 2011/0052549 | A1 | 3/2011 | Chin | |
| 2012/0064627 | A1 | 3/2012 | Khine | |
| 2012/0214189 | A1 * | 8/2012 | Shuler | C12M 41/46 435/293.1 |
| 2012/0222774 | A1 * | 9/2012 | Husnu | B65B 37/06 141/69 |
| 2013/0109081 | A1 | 5/2013 | Tsuchiya | |
| 2015/0267158 | A1 | 9/2015 | McKim | |
| 2017/0211025 | A1 | 7/2017 | McKim | |

FOREIGN PATENT DOCUMENTS

| | | | |
|---|---|---|---|
| EP | 1820846 | 8/2007 | |
| GB | 2493763 | 2/2013 | |
| JP | 2008-539787 | 11/2008 | |
| RU | 2296619 | 4/2007 | |
| WO | WO-2006097749 A1 * | 9/2006 | ............ B01L 3/5027 |
| WO | WO 2007/021343 | 2/2007 | |
| WO | WO 2010/023497 | 3/2010 | |
| WO | WO 2011/135339 | 11/2011 | |
| WO | WO 2014/165273 | 10/2014 | |
| WO | WO 2016/069917 | 5/2016 | |
| WO | WO 2017/027838 | 2/2017 | |

OTHER PUBLICATIONS

Berge, Stephen M. et al., *J. Pharm. Sci.* (1977), 66:1-19.
Majeed, Shoaib et al., "Characterization of the Vitrocell 24/48 in vitro Aeresol Exposure System Using Mainstream Cigarette Smoke," *Chemistry Central Journal*, (2014) 8(1) 62, 11 pages.
Lin, Christine et al., "The application of engineered liver tissues for novel drug discovery," *Expert Opinion on Drug Discovery* (2015) 10:519-540.
Extended European Search Report for Application No. 17188871.2 dated Mar. 15, 2018 (10 pages).
International Preliminary Report on Patentability for PCT/EP2018/073409 dated Nov. 26, 2019 (17 pages).
International Search Report and Written Opinion for PCT/EP2018/073409 dated Feb. 8, 2019 (25 pages).
Office Action issued in Russia for Application No. 2020112321 dated Jun. 1, 2022 (7 pages). English translation included.
Office Action issued in Japan for Application No. 2020-512556 dated Aug. 16, 2022 (4 pages). English translation included.
Office Action issued in Brazil for Application No. BR112020002747-2 dated Oct. 4, 2022 (5 pages). English translation included.
Office Action issued in Korea for Application No. 10-2020-7005269 dated Feb. 2, 2023 (14 pages).
Kim et al., 96 Well Format-Based Microfluidic Platform for Parallel Interconnection of Multiple Multicellular Spheroids, *Journal of Laboratory Automation*, 2015, 20(3), 274-282.
Office Action issued in China for Application No. 201880052722.8 dated Mar. 1, 2023 (11 pages). English translation included.
Zhang Peng, "Studies on Dual Melting Behavior, Solvent Resistance and Solvent-Induced Crystallization of Polyetheretherketone", Engineering Science and Technology I, China Doctoral Dissertation Full Text Database, No. 10, pp. B014-B042.

* cited by examiner

Units = mm

Units = mm

Units = mm

Units = mm

Units = mm

Units = mm

Well 1

| Well Diameter [mm] | Well height [mm] | Viscosity [dynes/cm2] | Flow [ml/min] |
|---|---|---|---|
| 11 | 3 | 0.00653 | 200 |

Shear Stress = 0.08

Well 2

| Well Diameter [mm] | Well height [mm] | Viscosity [dynes/cm2] | Flow [ml/min] |
|---|---|---|---|
| 16 | 3.5 | 0.00653 | 200 |

Shear Stress = 0.04

(a)

(b)

CELL CULTURE PLATE, DEVICES AND METHODS FOR IN VITRO EXPOSURE

This application is a U.S. National Stage Application of International Application No. PCT/EP2018/073409 filed Aug. 30, 2018, which was published in English on Mar. 7, 2019 as International Publication No. WO 2019/043130 A1. International Application No. PCT/EP2018/073409 claims priority to European Application No. 17188871.2 filed Aug. 31, 2017 and European Application No. 17208969.0 filed Dec. 20, 2017.

FIELD OF THE INVENTION

The present invention relates to a cell culture plate and a cell fluid exposure sampling device. One suitable cell type for use in the present disclosure is 3D organotypic cells or tissues. Fluid—such as a cell culture medium or a mixture of cell culture media—can be pumped or circulated through the cell culture plate which allows the cells or tissues to be simultaneously cultured in vitro. The cells can be exposed to one or more agents—such as aerosols—in order to study the effect of the agent on the cells and with the option of real time sampling of the cell culture media during the exposure.

BACKGROUND TO THE INVENTION

Toxicological studies using 2-dimensional cell culture systems have been used to examine the effects of one or more agents (for example, drugs) on cell survival and enzyme activity etc. While being able to grow cells in flat layers on plastic surfaces is straight forward and permits the study of several aspects of the cellular physiology and responses to stimuli, they do not reflect the real structure and architecture of an organ. In 2-dimensional monolayers, the extracellular matrix, the cell-to-cell and cell-to-matrix interactions, which are essential for the differentiation, proliferation and cellular functions are lost.

3-dimensional culture systems can form a functional tissue with similar features to those observed in vivo. As compared to the 2-dimensional culture systems, 3-dimensional cell culture allows cells to interact with their surroundings in all three dimensions and are more physiologically relevant. Such cells can show improvements in viability, proliferation, differentiation, morphology, response to stimuli, drug metabolism, gene expression and protein synthesis and the like. 3-dimensional cell culture can produce specific tissue-like structures and mimic functions and responses of real tissues in a manner that is more physiologically relevant than traditional 2-dimensional cell monolayers.

Several 3-dimensional tissues mimicking human organs are commercially available. Lung 3-dimensional organotypic tissues for example can be prepared using primary human cells grown at the air-liquid interface (ALI) where these cells will differentiate and form a functional tissue. These 3-dimensional tissues bear close morphological resemblance and metabolic characteristics to human bronchial tissues. Other 3-dimensional models have also been described, including 3-dimensional liver spheroid models. Liver spheroids can be composed of several cell types that were initially used in 2-dimensional cultures to determine the effects of treatments on liver cells.

Different techniques have been developed for 2-dimensional and 3-dimensional cell culture. 3-dimensional cell culture methods include the use of hanging drop plates, magnetic levitation, or biomaterial scaffolds. However, these techniques are often expensive and/or time consuming, and may not lend themselves to simultaneously culturing two or more different cell types. They can also be complicated to use, not autoclavable meaning that they cannot be reused, require a large liquid volume and flow for exchange of fluid, cannot be used with standard laboratory equipment, are often not capable of being waterproofed and are not amenable for high throughput or real-time sampling applications. The present invention seeks to provide improvements relating to cell culture and sampling of cell culture media.

SUMMARY OF THE INVENTION

In one aspect, there is disclosed a cell culture plate comprising at least two sequentially arranged wells and a channel adapted for fluid communication between the wells, wherein the channel is connected or coupled to a first pump via openings at each end of the channel, and wherein said first pump is operable to circulate fluid between the at least two wells. There is also disclosed a cell culture system or cell culture device comprising: (i) a cell culture plate comprising at least two sequentially arranged wells and a channel adapted for fluid communication between the wells; and (ii) a first pump, wherein the channel is connected or coupled to the first pump via openings at each end of the channel, and wherein the first pump is operable to circulate fluid between the at least two wells. Suitably, the channel is 3 millimetres or less in diameter or is a microfluidic channel.

Suitably, the pump is a peristaltic pump.

Suitably, the pump comprises a stepper motor or a brushless motor comprising an encoder.

Each motor can be controlled by a motor controller, the operation and the sensors of which can be controlled by a microcontroller. The operation of the microcontroller can be controlled by a wireless controller—such as a Bluetooth® controller—to facilitate use with a wireless device—such as a tablet.

Suitably, the channel is further configured to communicate fluid out of the cell culture plate.

Suitably, the channel is connected or coupled to a second pump, wherein said second pump is operable to communicate fluid out of the plate.

Suitably, the motor of the first pump and/or the second pump is housed in a waterproof box.

Suitably, the cell culture plate is fitted with a lid.

In certain embodiments, four pumps are used.

Suitably, the cell culture plate with the optional lid is housed in an incubator. The incubator can be configured to incubate at a defined fixed temperature—such as about 37° C. The incubator can be configured to incubate at different temperatures over a period of time, for example, during the course of an experiment.

Suitably, the cell culture plate and the pump(s) are both housed in an incubator.

Suitably, the temperature inside the incubator does not fluctuate by more than about 0.5° C. during use, for example, during the course of an experiment.

Suitably, the channel comprises two or more openings in the walls of the channel, wherein the two or more openings of the channel are coupled or connected to the wells.

Suitably, the channel is connected to the base or the top of the wells.

Suitably, the channel is connected to the top of the wells when liver spheroids are contained therein.

Suitably, the channel is configured to form a loop—such as U-bend.

Suitably, the wells form a linear arrangement of wells in the plate.

Suitably, the plate comprises 1, 2, 3 or 4 or more channels each connected to at least one pump that is capable of communicating fluid between the wells.

Suitably, the pump is located externally of the wells of the plate, suitably, wherein the pump is located adjacent the sequentially arranged wells arrangement of wells of the plate. When located externally, the pump can be connected to the plate via a connector—such as a Luer or Luer-lock connector or a simple tube connector.

Suitably, one or more of the wells comprise an insert for culturing cells, said insert comprising a permeable membrane that permits the passage of culture medium between the well and the insert.

Suitably, one or more of the wells comprise a surface coating.

Suitably, the permeable membrane is located on the base of the insert.

Suitably, the wells contain fluid, suitably, cell culture medium.

Suitably, the wells or inserts comprise cells.

Suitably, the wells are open and not sealed.

Suitably, the cells are 2-dimensional or 3-dimensional cell cultures.

Suitably, the cell culture medium contains one or more agents.

Suitably, the cell type in each of the wells is the same cell type or a different cell type.

Suitably, the different cell types are selected from adrenal, bladder, blood vessel, bone, bone marrow, brain, cartilage, cervical, corneal, endometrial, oesophageal, gastrointestinal, immune system, liver, lung, lymphatic, muscle, neural, ovarian, pancreatic, pituitary, prostate, renal, salivary, skin, tendon, testicular, and thyroid, suitably, wherein the cell types are lung cells or liver cells or neurons.

Suitably, the flow rate of the first pump is from about 10 μl per minute to about 1000 μl per minute. Suitably, the function of the first pump is controlled by a computer. Suitably, the wells of the cell culture plate or the cell culture plate is manufactured from polyether ether ketone (PEEK). PEEK is a species within the family of polyarylether ketones (PAEK).

Suitably, the wells of the cell culture plate or the cell culture plate comprise or consist of PEEK. Suitably, the channel is in fluid communication with a plate comprising one or more reservoirs capable of holding or storing a fluid.

Suitably, the base of the well comprises a discontinuous surface adapted to reduce or prevent the agglomeration of spheroids.

Suitably, the base of the wells is substantially circular in shape, suitably, wherein the diameter of the base is between about 6 mm±5% and about 16 mm±5%, suitably, wherein the diameter of the base is about 6 mm±5%, about 11 mm±5% or about 16 mm±5%.

Suitably, the discontinuous surface comprises a plurality of grooves in which the depth and width of the grooves corresponds to the largest diameter±10% of a spheroid.

Suitably, the depth and width of the plurality of grooves is between about 200 to about 1000 μm, suitably, between about 600 to about 1000 μm.

Suitably, the grooves form a plurality of concentric rings on the base of the well.

Suitably, the discontinuous surface comprises a plurality of holes having a closed bottom and an open top, the size of the holes corresponding in depth and width to be about 10% greater than the largest diameter of a spheroid.

Suitably, the well comprises cell culture medium for culturing spheroids.

Suitably, the well comprises individual spheroids trapped in the discontinuous surface of the well.

Suitably, the spheroids are lung spheroids.

Suitably, the flow of fluid from the inlet to the outlet of the well, when fluid is present therein, is between about 1 to about 500 μL/min, suitably, about 40 μL/min.

Suitably, the shear stress in the well is less than 0.1 dynes/cm$^2$.

Suitably, the base of at least one of the wells comprises a flat surface that is devoid of discontinuities.

Suitably, the at least one well comprises an insert positioned above the base of the well, suitably, wherein the insert is located on top of a permeable membrane located inside the well to form a surface that is capable of culturing a cell at an air/liquid interface.

Suitably, the depth of the at least one well comprising the flat surface that is devoid of discontinuities is different to the depth of the at least one well comprising the discontinuous surface, suitably, wherein the depth of the at least one well comprising the flat surface that is devoid of discontinuities is less than the depth of the at least one well comprising the discontinuous surface.

Suitably, the well comprises cell culture medium for culturing a cell at an air-liquid interface.

Suitably, the well comprises cells positioned on the permeable membrane, said cells being capable of growing at an air-liquid interface.

Suitably, the cells are lung cells.

Suitably, the channel is in fluid communication with a plate comprising one or more reservoirs capable of holding a fluid. In a further aspect, there is disclosed a cell culture device comprising the cell culture plate according to the present disclosure housed inside an incubator.

In a further aspect, there is disclosed a method for circulating a fluid between two or more sequentially arranged wells comprising: (a) providing the cell culture plate or the cell culture device described herein; (b) contacting the at least two wells with fluid; and (c) circulating the fluid through the wells of the plate.

A further aspect relates to a method for determining the effect of an agent on a cell comprising the steps of: (a) providing the cell culture plate or the cell culture device as described herein; (b) contacting the at least two wells of the cell culture plate with cells and cell culture medium; (c) circulating the cell culture medium through the wells of the plate; (d) exposing the wells of the plate to at least one agent; (e) removing and testing a sample of cell culture medium from one or more of the wells; and (f) determining the effect of the agent on the cells before and after exposure to the at least one agent.

A further aspect relates to a cell fluid exposure sampling device comprising: (a) the cell culture plate described herein; and (b) a sample plate comprising one or more wells for storing a plurality of samples, wherein said second pump is operable to communicate fluid from the cell culture plate towards the sample plate.

Suitably, the fluid is communicated to the sample plate using a multiple pipettor.

Suitably, the number of pipettes on the multi-head pipettor corresponds to the number of wells in the rows of the sample plate.

Suitably, the cell fluid exposure sampling device comprises a reservoir for storing fluid, wherein said reservoir is in fluid communication with the wells of the cell culture plate.

Suitably, the cell fluid exposure sampling device further comprises at least one further pump adapted to communicate culture medium from the reservoir to refill the wells of the cell culture plate.

Suitably, the at least one further pump is adapted to refill the wells of the cell culture plate with the same volume of culture medium as collected in the wells of the sample plate.

Suitably, the sampling device further comprises a computer controller operable to automatically control the operation of the device.

In a further aspect, there is provided a method for sampling a cell culture medium containing cells exposed to one or more agents comprising the steps of: (a) providing the cell fluid exposure sampling device described herein; (b) contacting at least one of the wells with cell culture medium comprising cells; (c) circulating the cell culture medium through the wells of the cell culture plate; (d) exposing the wells of the cell culture plate to at least one agent; and (e) sampling the cell culture medium from the cell culture plate, optionally wherein the cell culture medium is sampled in real time during exposure to the agent.

Suitably, in step (d) the wells of the cell culture plate are exposed to at least one agent at multiple time points.

Suitably, the volume of the culture medium sampled in step (e) is between about 50 ul to about 200 ul.

Suitably, the method comprises the further step (f) of determining the effect of the agent(s) on the sampled cells in the cell culture medium.

Suitably, the method comprises the further step (g) of determining the kinetics of the agent(s) on the exposed cells culture.

In a further aspect, there is disclosed the use of the cell culture plate as described herein for circulating a fluid between two or more wells.

In a further aspect, there is disclosed the use of the cell fluid exposure sampling device for sampling fluid from the wells of the cell culture plate, suitably in real-time.

In a further aspect, there is disclosed a cell culture device comprising or consisting of polyether ether ketone and containing an agent comprising: (i) a tobacco alkaloid; or (ii) a tobacco-specific nitrosamine; or (iii) an organic solvent with the proviso that the organic solvent is not a halogenated organic solvent or dimethyl sulfoxide or tetrahydrofuran; or a combination of two or more thereof.

There is disclosed a method for contacting a cell with one or more agents comprising: (i) contacting a cell with a cell culture device comprising or consisting of polyether ether ketone; (ii) culturing the cell; and (iii) contacting the cell contained in the cell culture device with one or more agents comprising: (i) a tobacco alkaloid; or (ii) a tobacco-specific nitrosamine; or (iii) an organic solvent with the proviso that the organic solvent is not a halogenated organic solvent or dimethyl sulfoxide or tetrahydrofuran; or a combination of two or more thereof.

In a further aspect, there is disclosed a method for reducing or inhibiting the absorbance of an agent with a cell culture device comprising or consisting of polyether ether ketone, comprising contacting the cell culture device with one or more agents comprising: (i) a tobacco alkaloid; or (ii) a tobacco-specific nitrosamine; or (iii) an organic solvent with the proviso that the organic solvent is not a halogenated organic solvent or dimethyl sulfoxide or tetrahydrofuran; or a combination of two or more thereof.

In a further aspect, there is disclosed the use of a cell culture device comprising or consisting of polyether ether ketone for reducing or inhibiting the absorbance of an agent, the agent comprising: (i) a tobacco alkaloid; or (ii) a tobacco-specific nitrosamine; or (iii) an organic solvent with the proviso that the organic solvent is not a halogenated organic solvent or dimethyl sulfoxide or tetrahydrofuran; or a combination of two or more thereof.

Suitably, the tobacco-specific nitrosamine is 4-(methylnitrosamino)-1-(3-pyridyl)-1-butanone.

Suitably, the tobacco alkaloid is selected from the group consisting of: nicotine, anabasine, nornicotine, anatabine, cotinine and myosmine or a combination of two or more thereof.

BRIEF DESCRIPTION OF THE DRAWINGS

FIG. 21(*b*) shows non-agglomerated spheroids in individualised form obtained according to the present disclosure.

SOME ADVANTAGES

Figure 1:
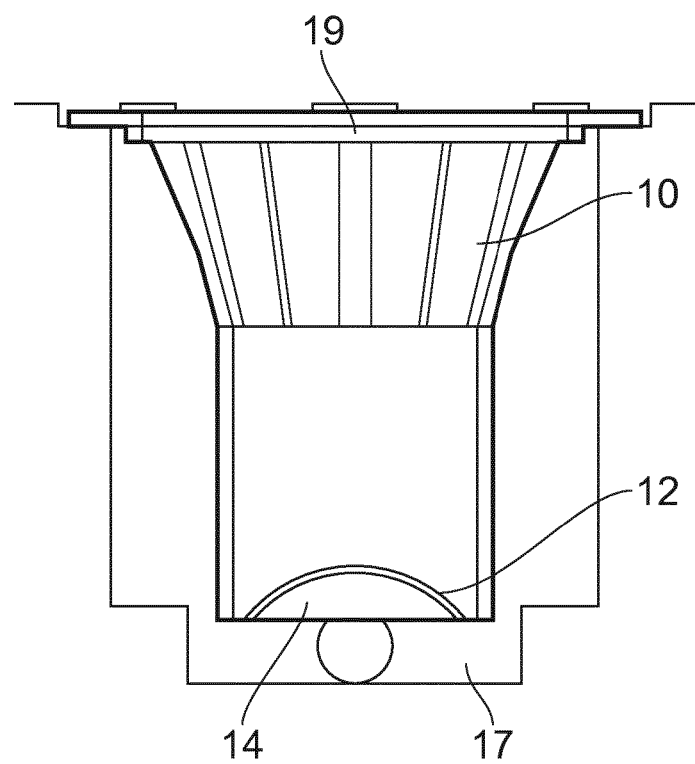
FIG. 1 illustrates an insert for use in the present disclosure.

The present disclosure can use standard cell culture plates which simplifies design, reduces cost and provides a solid basis for experimentation as standard cell culture plates are widely used in laboratories. For example, analysis of the standard cell culture plate can be carried out using standard laboratory equipment. Suitably, the standard cell culture plate comprises two or more or a plurality of wells that are substantially circular in shape. Suitably, the diameter of the base of the wells is between about 6 mm±5% and about 16 mm±5%, suitably, wherein the diameter of the base is about 6 mm±5%, about 11 mm±5%, or about 16 mm±5%. In one embodiment, the diameter of the base of the wells is between about 6 mm±5% (for example, about 6.4 mm) and about 16 mm±5% (for example, about 15.5 mm).

The cell culture plate/cell fluid exposure sampling device can be used with standard cell culture inserts which simplifies design and reduces the cost of the cell culture plate.

The cell culture plate/cell fluid exposure sampling device can be used to culture and study 3-dimensional cell cultures.

The cell culture plate/cell fluid exposure sampling device overcomes limitations of conventional cell culturing techniques. For example, it can more closely mimic the natural micro-environment for the cells.

Different 3-dimensional cell cultures can be cultivated on the same plate which permits the connection of different cell types together so the interaction between the cells can be determined.

The cell culture plate/cell fluid exposure sampling device can reduce the risk of contamination as it is autoclavable.

The cell culture plate/cell fluid exposure sampling device can be prepared without the use of glue which can improve biocompatibility.

The cell culture plate and the corresponding pump(s) used to circulate fluid between the wells can be housed together in an incubator. The incubator can remain closed during use and the cells can remain undisturbed. The flow rate of fluid that is set by the pumps can be modulated (for example, via Bluetooth®) without disturbing the cells. As the incubator can remain closed during use, the temperature inside the incubator can remain stable to minimise temperature fluctuations. As the cell culture plate and the corresponding pump(s) are housed together in the same incubator, wires running between the inside and outside of the incubator can be minimised and this can improve the seal of the incubator and further reduce temperature fluctuations. Only one cable will typically be required outside of the incubator to connect the pump to an energy supply, although battery operated pumps could be used if required. This can simplify the design of the incubator comprising the cell culture plate and the corresponding pump(s) which makes it less cumbersome and easier to use. The circulated fluid—such as cell culture medium—can be mixed automatically which can permit improved culture of cells/tissues.

The wells of the cell culture plate can be open and not sealed. During use, tissues or cells in the wells can be exposed to ambient air present in the incubator. Such a system allows the medium to equilibrate with the air present in the incubator, maintaining the pH of the medium at a physiological level and ensuring that the gases emitted by the tissues are removed from the medium. This configuration is particularly desirable when using tissues or cells grown at the air-liquid interface which are more dependent on ambient air humidity and gas concentration.

The cell culture plate/cell fluid exposure sampling device allows two or more cell types to be cultured simultaneously. This allows the interaction of the cells with each other to be studied.

The cell culture plate/cell fluid exposure sampling device allows the skilled person to study how a metabolised agent from a first cell type impacts a second cell type.

The cell culture plate/cell fluid exposure sampling device allows the skilled person to study how a metabolised agent from a second cell type impacts a first cell type.

The cell culture plate/cell fluid exposure sampling device allows the impact of metabolised agents from different cell types, including combinations of different cell types, to be studied.

The cell culture plate/cell fluid exposure sampling device can be adapted for use in high throughput assays—such as high throughput sampling or screening assays.

The cell culture plate/cell fluid exposure sampling device can be adapted for use in real time assays—such as real time sampling or screening assays.

DETAILED DESCRIPTION

The practice of the present disclosure employs, unless otherwise indicated, conventional techniques of engineering, micro-engineering, microbiology, cell biology and biochemistry. Such techniques are explained fully in the literature, such as, in Molecular Cloning: A Laboratory Manual, second edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. CelMs, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, I B. Griffiths, and D. G. Newell, eds., 1993-8) J. Wiley and Sons; Methods in Enzymology (Academic Press, Inc.); Current Protocols in Molecular Biology (F. M. Ausubel et al., eds., 1987); PCR: The Polymerase Chain Reaction, (Mullis et al., eds., 1994). Procedures employing commercially available kits and reagents will typically be used according to manufacturer-defined protocols unless otherwise indicated.

The technical terms and expressions used herein are generally to be given the meaning commonly applied to them in the pertinent art of molecular biology, microbiology, cell biology and biochemistry. All of the following term definitions apply to the complete content of this application.

As used herein, the singular forms "a", "an", and "the" include both singular and plural referents unless the context clearly dictates otherwise.

The term "and/or" means (a) or (b) or both (a) and (b).

The terms "comprising", "comprises" and "comprised of" as used herein are synonymous with "including", "includes" or "containing", "contains", and are inclusive or open-ended and do not exclude additional, non-recited members, elements or method steps.

The term "consisting of" means that additional components are excluded and has the recited elements only and no more.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Cell Culture Plate

A cell culture plate for use in the present disclosure can be manufactured in various formats—such as in 24, 48 or 96-well formats—and can be readily selected by the skilled person based upon the size and choice of the experiment that it is intended to carry out. Suitably, the cell culture plate for use in the present disclosure is a 24, 48 or 96-well format cell culture plate. Typically, the cell culture plate measures about 12 cm in length and about 8 cm in width.

The cell culture plate will typically be in the form of a flat plate comprising a plurality of wells. In general, the whole plate is rectangular.

Suitably, the diameter of the base of the wells is between about 6 mm±5% and about 16 mm±5%, suitably, wherein the diameter of the base is about 6 mm±5%, about 11 mm±5%, or about 16 mm±5%. In one embodiment, the diameter of the base of the wells is between about 6 mm±5% (for example, about 6.4 mm) and about 16 mm±5% (for example, about 15.5 mm).

The capacity of each well can be between about 300 μL and about 3400 μL, or between about 350 μL and about 3400 μL, or between about 370 μL and about 3400 μL. Typically, the volume of fluid that is circulated in the cell culture plate will be between about 2.5 mL and about 12 mL—such as about 8 mL. The cell culture plate is configured to contain at least two sequentially arranged wells. The cell culture plate can be configured to contain at least two linearly arranged wells.

Typically, the wells in the cell culture plate will be arranged in rows and columns. For example, a 24 well plate can be configured in 6 linear rows of 4 adjacent wells in each row. By way of further example, a 48 well plate can be configured in 8 linear rows of 6 adjacent wells in each row. By way of further example, a 96 well plate can be configured in 12 linear rows of 8 adjacent wells in each row. Cell culture plates can even be manufactured or custom built, if required, to provide the desired number of wells in the plate.

It is not necessary for every well in the plate to be used. Provided that at least two sequentially arranged wells are used in the cell culture plate then this will suffice for carrying out an experiment in accordance with the present disclosure.

The wells of the cell culture plate will typically be open and not sealed which can assist in the culturing/maintenance of cells and the circulation of aerosol.

The cell culture plate can be fitted with a lid on top of the plate which helps to reduce the risk of contamination in the wells. The lid is preferably not sealed to the plate so that air can circulate inside the plate which can also assist in the culturing/maintenance of cells and the circulation of aerosol.

The cell culture plate can be made from polytetrafluoroethylene (PTFE), stainless steel (for example, 316L/1.4435), PEEK, polypropylene or polysulfone or a combination of two or more thereof. A coating—such as a coating of parylene—can be applied to any of the PTFE, stainless steel (for example, 316L/1.4435), PEEK, polypropylene or polysulfone materials.

In certain embodiments, the use of PEEK is preferred as it has the advantage of not being absorbent towards nicotine and NNK, as described herein.

Cell culture plates can be designed by computer-aided design (CAD) if required or they are commercially available. CAD plates can be produced by micro mechanical machining using methods that are well known in the art.

Suitably, the cell culture plate is a single piece cell culture plate. As a single piece, the cell culture plate is devoid of layers. As a single piece, the cell culture plate is devoid of glue. As a single piece, the cell culture plate is devoid of layers and glue. This can assist in the sterilisation of the cell culture plate as it can be completely autoclaved.

In one embodiment, the cell culture plate is a microfluidic cell culture plate which is widely available in the art. For example, a M04S microfluidic cell culture plate is available from Cellasic, California, USA, and contains 4 independent wells, each well is about 2.8 mm in diameter with a 120 micron height. The dimensions of this plate are about 8.5 cm wide, about 12.7 cm in length and about 1.4 cm in height.

In certain embodiments, the length of the cell culture plate is about 10 cm or greater in length, or about 11 cm or greater in length, or greater than about 12 cm in length. In certain embodiments, the length of the cell culture plate is less than about 10 cm in length—such as about 9 cm in length, about 8 cm in length, about 7 cm in length, about 6 cm in length or about 5 cm in length.

The cell culture plate is adapted to allow fluid communication between at least two sequentially arranged wells. This can be achieved by forming at least one hole in each of the wells of the cell culture plate and then connecting each of the wells via the hole(s) to a channel (for example, a conduit or pipe). In one embodiment, the channel(s) are directly machined or embedded inside the cell culture plate to provide for the connection of the at least two wells together. Suitably, the channel(s) run under the wells of the cell culture plate. The channel(s) can connect to the bottom or top of the wells, as required. The channel can be about 3 mm, about 1.6 mm or about 1 mm or less in diameter. The channel can have a circular diameter to reduce the formation of air bubbles. The channel can be a microfluidic channel which will have a diameter of less than 1 mm. The use of microfluidic channels is well known to the person skilled in the art.

The channel contains openings at each end. Typically, each end of the opening is connected to the same pump. Accordingly, each end of the opening will terminate in the same pump.

Various kinds of connector can be used to connect the channel to a first pump. One example is a Luer connector—such as a Luer-lock connector—or a simple tube connector. The use of a Luer connector is advantageous as they are readily available, easy to mount and can offer improved sterility and tightness.

A portion of the channel that communicates fluid towards or away from the first pump is referred to herein as a 'fluid transmission channel'. The walls of the fluid transmission channel will normally be sealed aside from the opening at one end which can be connected or coupled to a first pump. In other words, the walls of this portion of the channel will be devoid of any openings. Another portion of the channel is referred to herein as a 'well communication channel' as it communicates fluid to each well via openings in the walls of the channel. The number of openings in the walls of the well communication channel will depend upon the number of wells that fluid is to be communicated to. Typically, the openings in the walls of the well communication channel will be located in the upper part of the well communication channel. The well communication channel will usually be connected to either the base or the top of the wells. In certain embodiments, it is preferred that the well communication channel is connected to the top of the wells when liver spheroids are contained therein. The well communication channel can communicate fluid towards or away from the pump. The fluid transmission channel and the well communication channel will generally be configured in a substantially linear arrangement and can be arranged substantially parallel to each other.

The channels can be in the form of tubes—such as flexible tubes. The channels can therefore be made of tubing—such as flexible tubing or silicon tubing or Pharmed tubing. A loop or U-bend joins the fluid transmission channel and the well communication channel. The loop is configured to communicate fluid away from the pump and then to return it back towards the pump.

The loop can be located internally or externally of the cell culture plate. When the loop is located externally off the cell culture plate then a connector—such as a Luer connector or Luer-lock connector or a simple tube connector—can be used to seal and engage the loop to the cell culture plate.

Tubing can be used to connect the different channels together—such as silicon tubing or Pharmed tubing.

Figure 9:
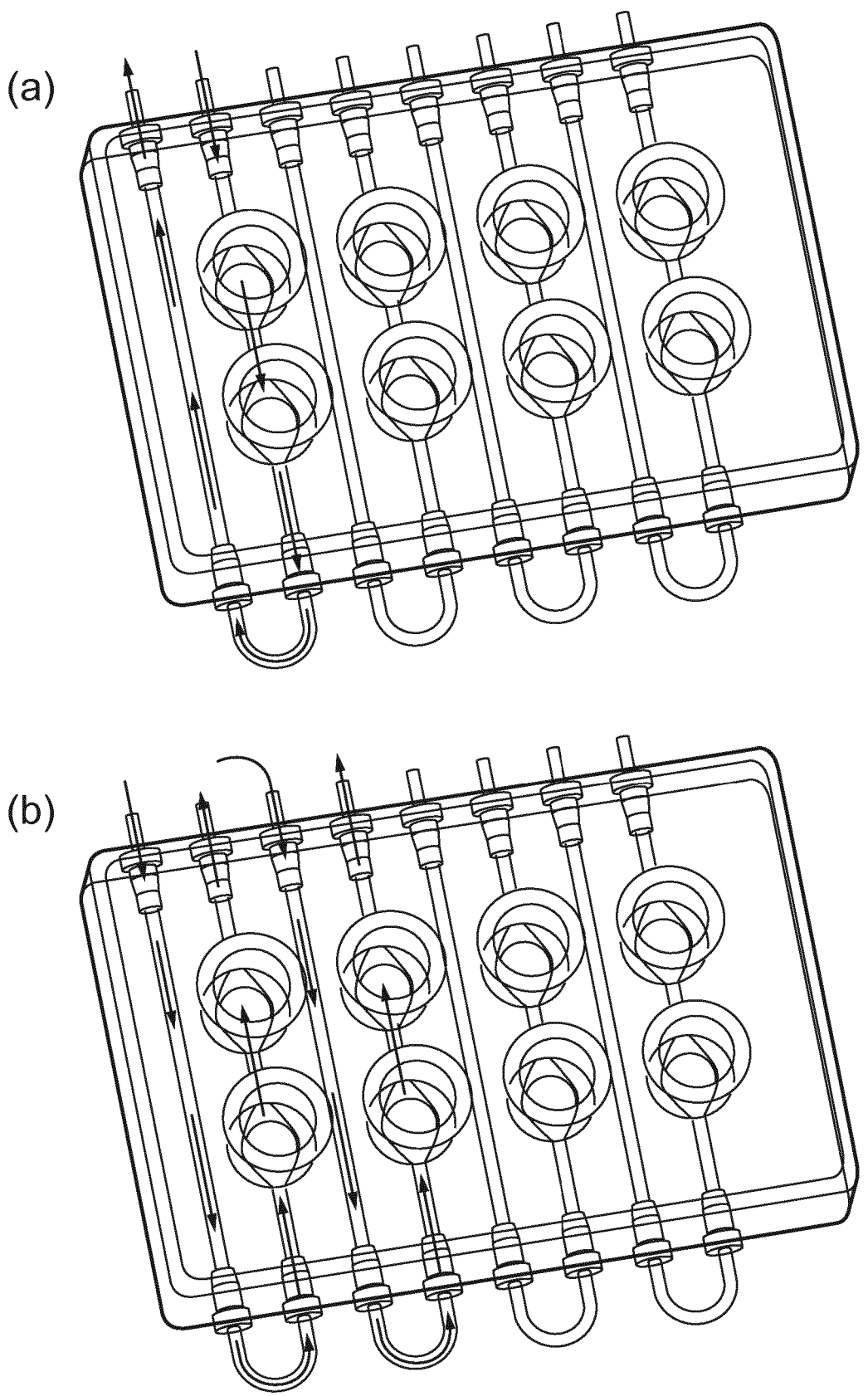
FIG. 9(a) illustrates one embodiment of a cell culture plate of the present disclosure comprising one channel with 2 wells and one channel without wells that permits the return of fluid. A connector is used to connect a tube to allow fluid to pass from the channel with the 2 wells, to the channel without wells and then back to a single pump.
FIG. 9(b) illustrates an embodiment in which more than 2 wells are connected to each other to allow more cells or tissues to be connected together. It is therefore possible to connect 2, 4, 6 or 8 wells etc. Each end of the channel is connected to the same single pump.

When fluid is carried in the channel, it can be carried from the pump and then returned back to the pump. The fluid can be circulated in a clockwise or anti-clockwise fashion through the wells as required. The first pump is typically configured to be orientated on the opposing side of the cell culture plate to the loop, which returns fluid through the fluid transmission channel or the well communication channel. The first pump and the loop can be arranged on opposing sides of the cell culture plate in a substantially linear arrangement. Whilst in certain embodiments, the fluid is communicated from the first pump, to the fluid transmission channel and to the well communication channel via the loop and back to the first pump (see FIG. 2), it also contemplated that the fluid is communicated from the first pump to the well communication channel and to the fluid transmission channel via the loop and back to the first pump (see FIGS. 3c and 9a, for example). It is also contemplated that fluid is communicated from the first pump to a first fluid transmission channel and then to a first well communication channel via a first loop and then, via a second loop, to a second fluid transmission channel and to a second well communication channel via a third loop (see FIG. 9b, for example) and then back to the first pump.

The cell culture plate comprising the at least two sequentially arranged wells and the channel adapted for fluid communication between the wells that is connected or coupled to a first pump via openings at each end of the channel can form a circuit for circulation of fluid between the at least two wells. The fluid can circulate between the wells via the channel and the pump. In certain embodiments, the plate is composed of 1, 2, 3 or 4 or more circuits. Each circuit can comprise 2 or 4 or 6 or 8 or more wells. One or more of the wells can be designed to specifically permit the placement of inserts—such as Transwell™ inserts—in the wells. The plate can be of various sizes, as required—such as a standard 24- or 96-well plate. Suitably, the standard plates comprise two or more or a plurality of wells that are substantially circular in shape.

The 2 or 4 or 6 or 8 wells per circuit can be interconnected by a channel—such as a microchannel—running along their bottom. On one side of each circuit, two connectors can be present for connecting each circuit to a peristaltic pump. Once the circuits are filled with medium and connected to the pump, the design of the plate ensures a level of circulating medium sufficient to make contact with an insert in the first well and to cover the spheroids present in the second well.

Two circuits can also be joined together (by connecting the outgoing connector of one circuit to the incoming connector of the second circuit) to interconnect up to 4 tissues.

It is also possible to change the way medium circulates in the circuits: the circuits can be in a closed loop where medium recirculates or open with medium making a single pass through each well. In the latter case, a first tube can be connected to a reservoir filled with medium on the first extremity and to the incoming connector of a circuit on the second side. The outgoing connector of this last circuit will then be connect to a tube passing through a pump and rejecting medium within a collector.

The cell culture plate can be open to ensure optimal gas exchange between the tissues within the plate and the air present in an incubator. In certain embodiments, the cell plate is fitted with a lid or a cover which allows for air circulation identical to a standard cell culture plate.

Figure 2:
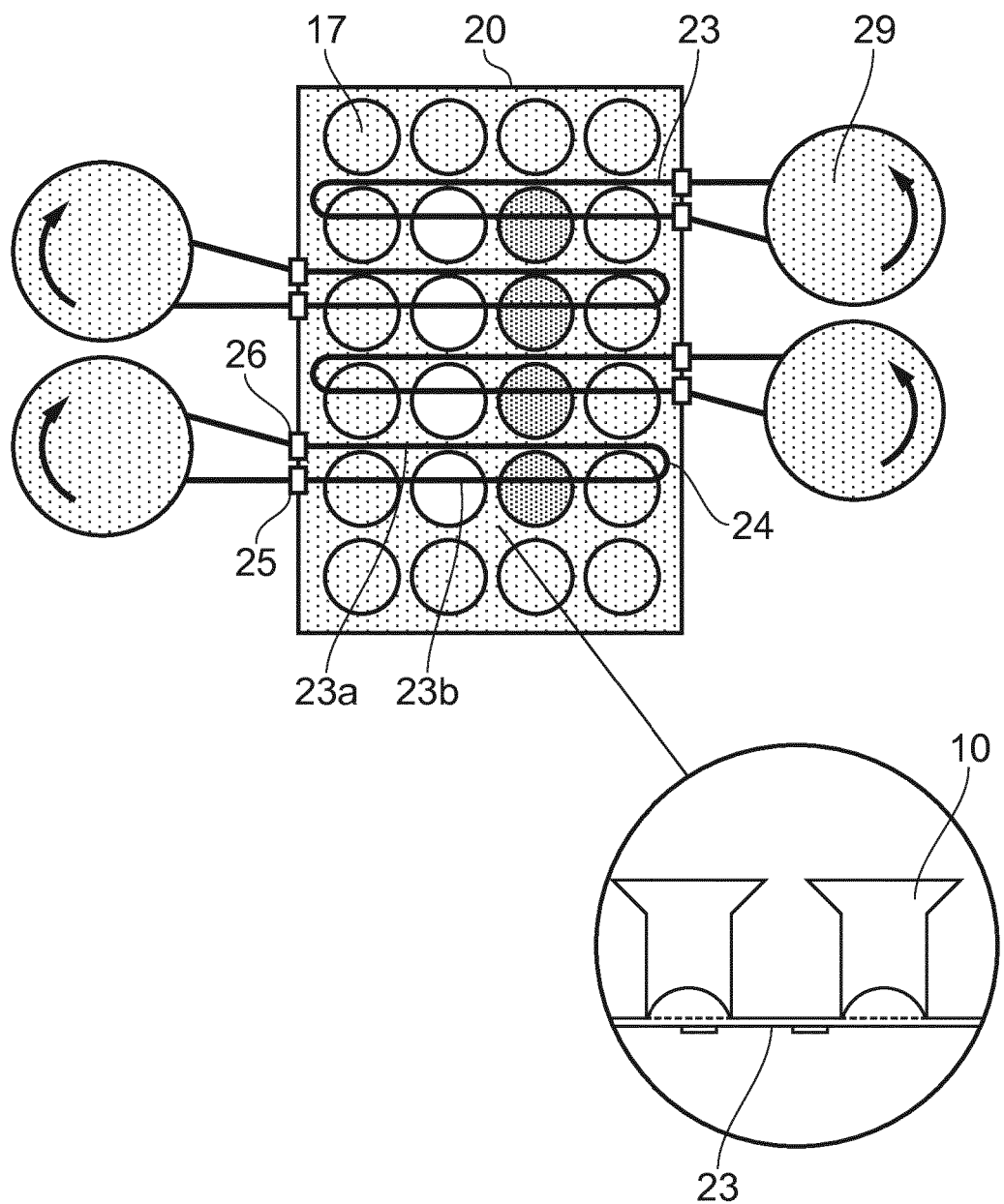
FIG. 2 illustrates one embodiment of a cell culture plate of the present disclosure.

Turning to the figures, specific non-limiting embodiments of a cell culture plate are described in more detail. FIG. 2 illustrates one embodiment of a cell culture plate 20 containing 24 wells 17 configured in 6 rows containing 4 linearly arranged wells 17. 4 of the rows are each configured to allow fluid communication between each of the 4 linearly arranged wells 17 via a channel 23. The fluid transmission channel 23a and the well communication channel 23b are shown. The channel can comprise an inlet opening 26 to allow fluid communication into the cell culture plate 20 and an outlet opening 25 to allow fluid communication out of the cell culture plate 20 and back to the pump 17. At least two of the wells 17 will each contain at least one opening to allow the well communication channel 23b to connect thereto. The channel 23 can be configured to form a loop 24 at one end thereof. The loop 24 can be contained internally of the cell culture plate 20 or externally of the cell culture plate 20, as exemplified in FIG. 3 which illustrates an externally located loop 39. When positioned externally, the loop 24 will be connected to the cell culture plate 20 via connectors that join the loop to the cell culture plate 20. Returning to FIG. 2, the channel 23 is connected at one end to at least one pump 29 via the openings 25, 26 at each end of the channel 23 to pump fluid between the wells 17. The ends of the openings 25, 26 are connected to the pump 29 via connectors 28, which can be seen in FIG. 3. When two or more pumps 29 are used, they can be conveniently configured in a staggered configuration on opposing sides of the cell culture plate 20.

Figure 3:
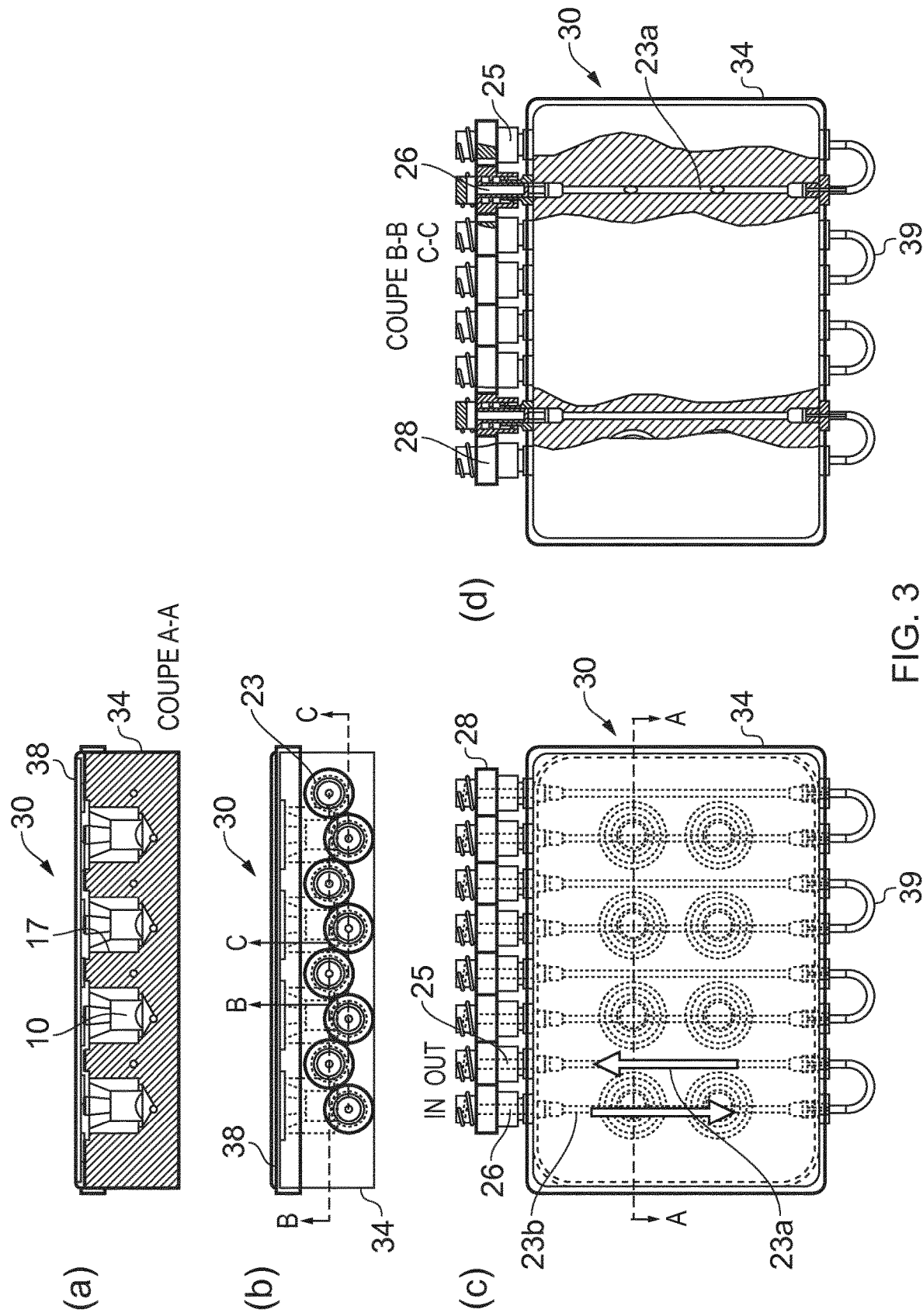
FIG. 3 illustrates a further embodiment of a cell culture plate of the present disclosure.

FIG. 3 illustrates a further embodiment of the cell culture plate 20. FIG. 3a illustrates a cross section A-A through the wells 17 illustrated in FIG. 3c illustrating the configuration of the wells 17 and inserts 10 in the plate. FIG. 3b illustrates cross sections B-B and C-C through the channels 23 contained in the cell culture plate 20 shown in FIG. 3d. FIG. 3c illustrates the direction of circular flow of fluid when contained in the channel 23. Fluid is communicated from the pump to the well communication channel 23b and to the fluid transmission channel 23a via the loop and back to the pump (not shown). A waterproof housing 34 can be used to contain the cell culture plate 20. The waterproof housing can contain a lid 38. In the illustrated embodiment, the connectors 28 and the loop 39 of the channels 23 are housed outside of the waterproof housing. FIG. 3d illustrates the linear configuration of the fluid transmission channel 23a.

Figure 4:
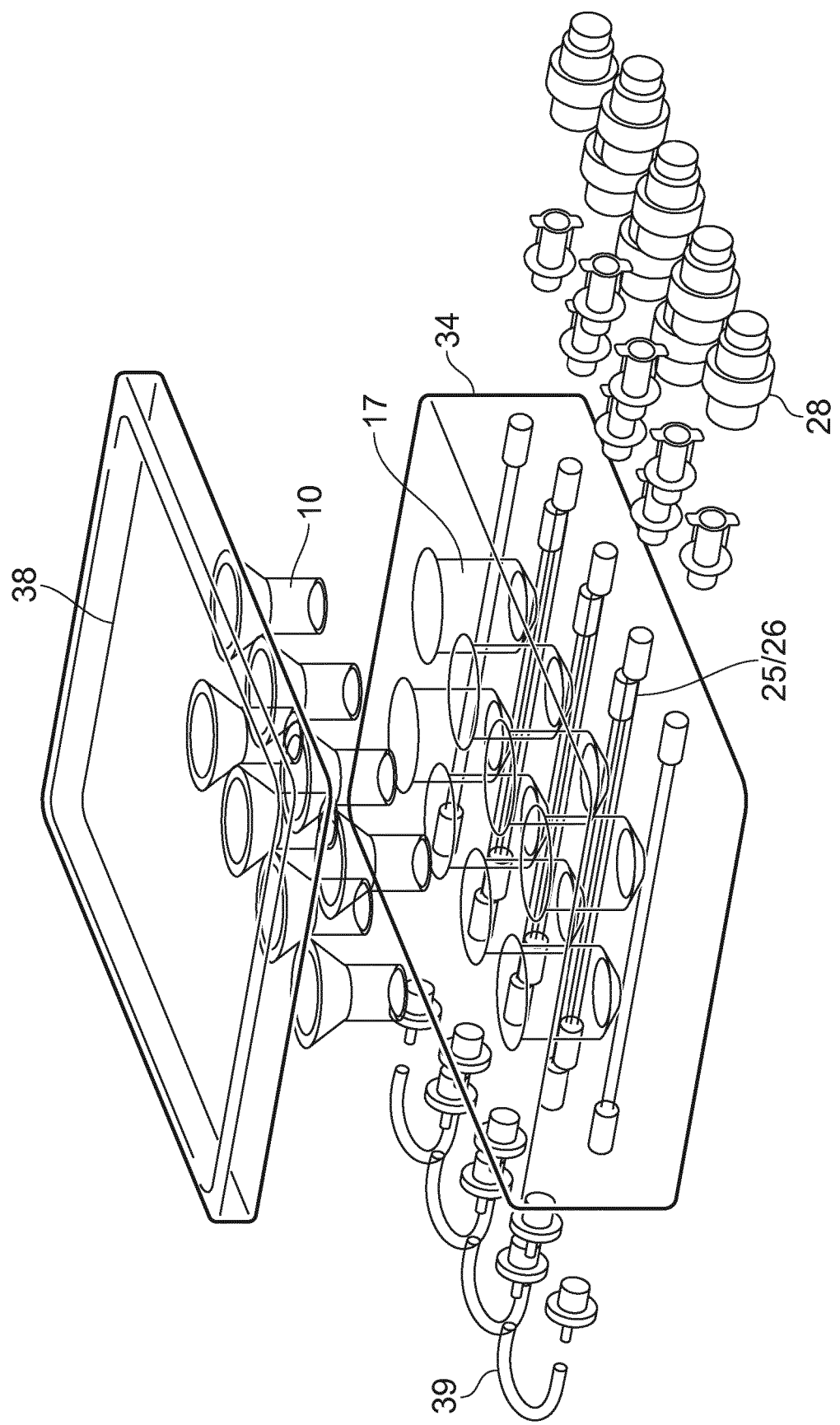
FIG. 4 is a 3-dimensional representation of the cell culture plate depicted in FIG. 3.

FIG. 4 is a 3-dimensional representation of the cell culture plate depicted in FIG. 3.

Figure 5:
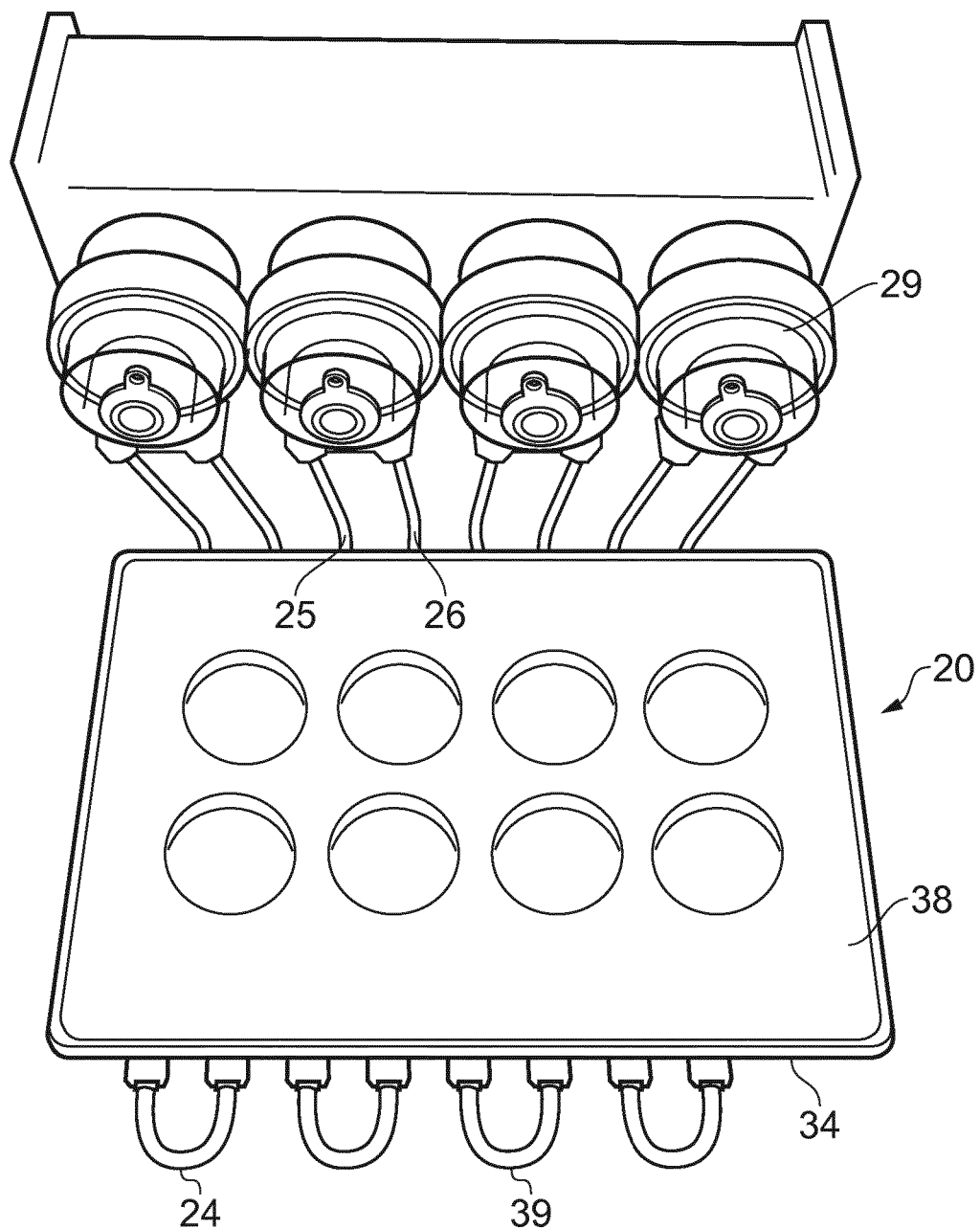
FIG. 5 is a photograph of a constructed cell culture plate as depicted in FIG. 4.

FIG. 5 is a photograph of a constructed cell culture plate as depicted in FIG. 4.

Figure 6:
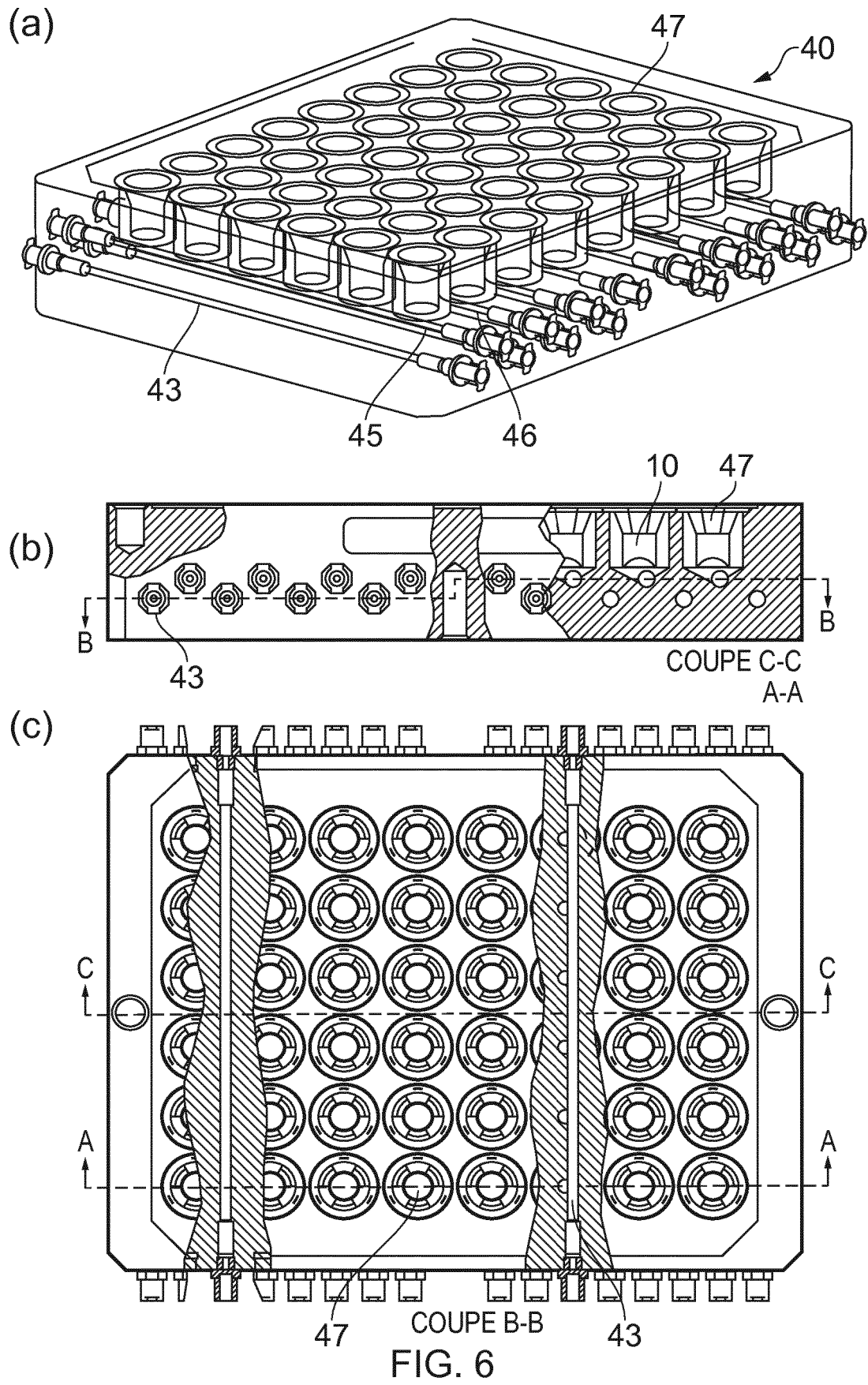
FIG. 6 illustrates a further embodiment of a cell culture plate of the present disclosure.

FIG. 6 illustrates a further embodiment of a cell culture plate 40. FIG. 6(a) illustrates a cell culture plate 40 containing 48 wells configured in 8 rows containing 6 linearly arranged wells 47. Each of the rows are configured to allow fluid communication between each of the 6 linearly arranged wells 47 via a channel 43. The channel visible in this Figure is a fluid transmission channel. The channel can comprise an inlet opening 45 to allow fluid communication into the wells 47 and an outlet opening 46 to allow fluid communication out of the wells 47. FIG. 6(b) is a cross section through the plate illustrated in FIG. 6(a). FIG. 6(c) is a plan view of the plate illustrated in FIG. 6(a).

Figure 7:
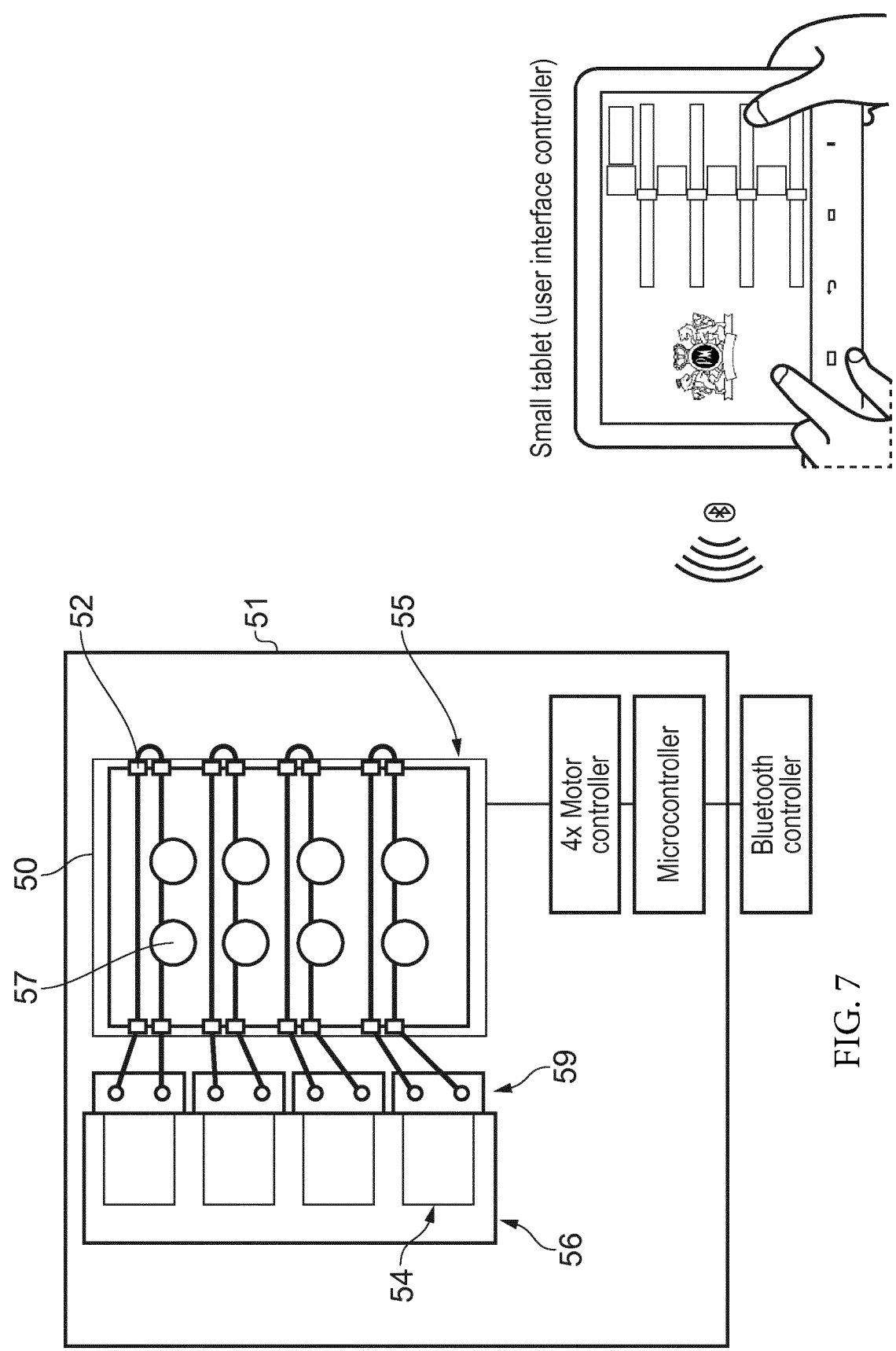
FIG. 7 illustrates a further embodiment of a cell culture plate of the present disclosure in which the cell culture plate (which can be fitted with an optional lid) and the pump(s) is housed in an incubator.

FIG. 7 illustrates a further embodiment of a cell culture plate 50 containing a total of 8 wells 57 configured in 4 rows containing 2 linearly arranged wells 57 in each row. Each row is connected to a separate pump 59 comprising a motor 54. Each pump can have a different pumping parameter. Fluidic connectors 52 are shown. The motors of the pump(s) can be contained in a sealing box 56 which can be waterproofed. The sealing box 56 can include a lid. The cell culture plate can be placed on a plate support 55. Each motor 54 can be controlled by a motor controller, the operation of which can be controlled by a microcontroller. The operation of the microcontroller can be controlled by a wireless controller—such as a Bluetooth® controller—to facilitate use with a wireless device—such as a tablet. The cell culture plate and the pump(s) can together be housed in an incubator 51.

In certain embodiments, the flow of fluid through the well is between about 1 to about 100 μL/min.

In certain embodiments, the flow of fluid through the well is between about 1 to about 500 μL/min.

In certain embodiments, the flow of fluid through the well is between about 10 to about 400 μL/min or about 10 to 250 μL/min or about 10 to 100 μL/min.

In certain embodiments, the flow of fluid through the well is about 40 μL/min.

When more than one pump is used, one or more of the different pumps can have different flow rates. When more than one pump is used, each of the different pumps can have different flow rates. Accordingly, the flow rates in each circuit can be the same or different.

As will be appreciated by the skilled person, when fluid flows over a solid boundary it will incur a shear stress on that boundary, which may lead to the perturbation of cells exposed to the shear stress. In the context of the present disclosure, when fluid moves through the well, a shear stress will be created. It is desirable that the shear stress in the well is less than about 0.1 dynes/cm$^2$—such as about as 0.08 dynes/cm$^2$ or less or 0.04 dynes/cm$^2$ or less—as this does not cause perturbation of cells exposed to the shear stress. The shear stress can be different in different wells. For example, a well with a discontinuous surface can have a shear stress of about 0.04 dynes/cm$^2$. For example, a well with a flat and non-discontinuous surface can have a shear stress of about 0.08 dynes/cm$^2$. Suitably, the shear stress in the well with a discontinuous surface is lower than a well with a flat and non-discontinuous surface.

So that optical analysis can be used for screening, the bottom of the well can be made of a material having a total light transmittance of 70% or 80% or 90% or more.

The depth of the plurality of wells does not have to be the same across the cell culture plate and it is contemplated that the wells can have different depths. The channel connecting the at least two wells can be at the same height such that the channel is located at different distances from the base of the at least two wells. This configuration ensures that the flow of fluid into the well does not perturb or disturb the spheroids, whilst ensuring that the fluid can still pass through the permeable membrane of the insert. In one embodiment, the well(s) for culturing spheroids have the greatest depth. In one embodiment, the well(s) for culturing spheroids have a depth that is greater than the well(s) for culturing cells other than spheroids. In one embodiment, the well(s) for culturing spheroids have a depth that is greater than the well(s) containing an insert.

Figure 23:
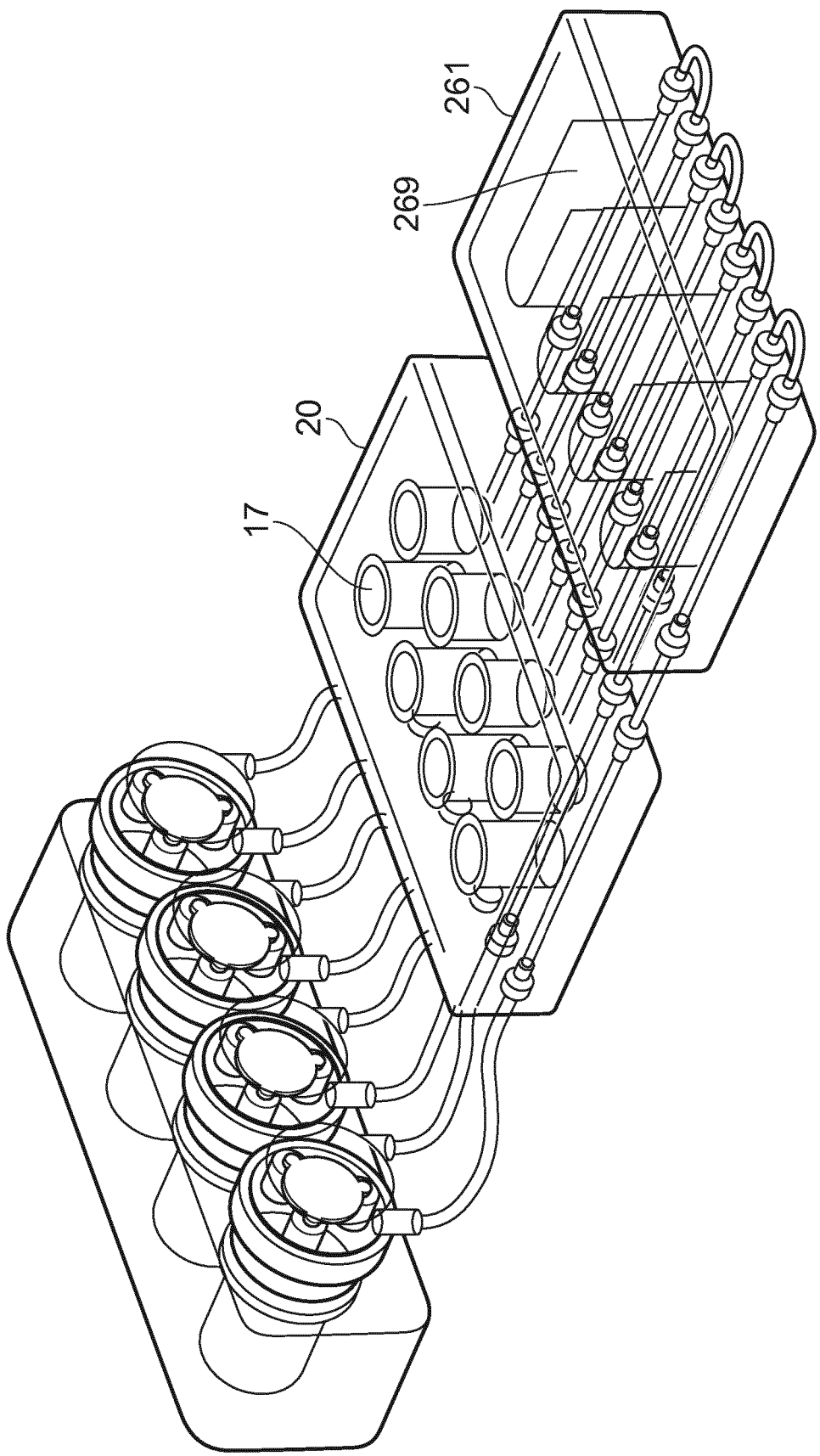
FIG. 23 shows a cell culture plate connected to a reservoir plate which can be used to increase the volume of circulating fluid.

If required, the cell culture plate can be used together with a reservoir plate 261, as depicted in FIG. 23. The reservoir plate comprises one or more fluid reservoirs 269. The fluid reservoir(s) 269 can be configured to contain fluid. This Figure illustrates one embodiment of a cell culture plate 20 containing 8 wells 17 configured in 4 rows containing 2 linearly arranged wells 17, although it will be appreciated that other configurations of wells can be readily used. Rather than the channels 23 forming a loop on or adjacent to the cell culture plate the channels pass into the one or more fluid reservoirs 269 of the reservoir plate 261. The channels form a loop on or adjacent to the reservoir plate 261. Fluid is communicated from the one or more fluid reservoirs 269 to the cell culture plate and circulated. The reservoir plate 261 can be used to increase the volume of fluid. Typically, the volume of fluid used in this configuration will be between about 8 mL and about 12 mL.

Sample Plate

A sample plate for use in the present disclosure can be manufactured in various formats—such as in 24, 48 or 96-well formats—and can be readily selected by the skilled person based upon the size and choice of the experiment that it is intended to carry out.

The sample plate is also configured to contain at least two sequentially arranged wells. The sample plate can be configured to contain at least two linearly arranged wells.

Typically, the wells in the sample plate will be arranged in rows and columns. For example, an 8 well plate can be configured in 4 linear rows of 2 adjacent wells in each row. In this configuration, individual pumps can be used for each row. Each pump can have a different pumping parameter.

By way of further example, a 24 well plate can be configured in 6 linear rows of 4 adjacent wells in each row.

By way of further example, a 48 well plate can be configured in 8 linear rows of 6 adjacent wells in each row. In this configuration, a single pump can be used for all rows such that the same pumping parameter is used across all rows. In another configuration, 3 pumps are used. The same pumping parameter can be used across all rows.

By way of further example, a 96 well plate can be configured in 12 linear rows of 8 adjacent wells in each row. Sample plates can even be manufactured or custom built, if required, to provide the desired number of wells in the sample plate.

Provided that the sample plate comprises at least two sequentially arranged wells then it can be used in accordance with the present disclosure, although the use of larger plates is preferred so that more experiments can be carried out. It is not necessary for every well in the sample plate to be used. Provided that at least two sequentially arranged wells are used in the sample plate then this will suffice for carrying out an experiment in accordance with the present disclosure.

The sample plate can be fitted with a lid on top of the plate which helps to reduce the risk of contamination.

The sample plate can be made from polytetrafluoroethylene (PTFE), stainless steel (for example, 316L/1.4435), polyetheretherketone (PEEK), polypropylene, polysulfone or PTFE or a combination of two or more thereof, optionally with a coating of parylene.

In certain embodiments, the use of PEEK is preferred as it has the advantage of not being absorbent towards nicotine and NNK, as described herein.

Samples plates can be designed by computer-aided design (CAD) if required or they are commercially available. CAD plates can be produced by micro mechanical machining using methods that are well known in the art.

In one embodiment, the sample plate is a microfluidic cell culture plate which is widely available in the art. For example, a M04S microfluidic cell culture plate is available from Cellasic, California, USA, and contains 4 independent wells, each well is about 2.8 mm in diameter with an about 120 micron height.

Unlike the cell culture plate, the sample plate will typically be devoid of a channel in the sample plate as fluid can be communicated to the wells of the sample plate via a pipettor—such as an automated pipettor. In addition, the side walls and the base of the wells of the sample plate will usually be sealed as fluid communication with a channel is not required.

The cell culture plate and the sample plate can have the same number of rows of wells or the sample plate can have a larger number of rows of wells, as discussed below.

Pump

In one embodiment, the pump(s) for use in the present disclosure is a positive displacement pumps that is operable to circulate fluid, such as a peristaltic pump. As understood in the art, a peristaltic pump is a pump used for moving a fluid. The fluid is contained within the channel described herein—the channel can be a flexible tube that fits inside a pump casing. In the alternative, if the channel is directly machined (for example, embedded) into the plate then an adaptor can be used to connect the machined or embedded channel to the pump. A rotor attached to the external circumference thereof compresses the flexible tube or channel. As the rotor turns, the part of the tube or channel under compression is pinched closed to force the fluid through the tube or channel.

A first (circulating) pump can be used to control the flow of fluid in the cell culture plate. A second (sample) pump can be used to move fluid from the cell culture plate to the sample plate.

In one embodiment, the flow rate of the first pump is between about 10 μl per minute to about 1000 μl per minute.

In one embodiment, the flow rate of the second pump is between about 10 ul per minute to 2000 ul per minute. The flow rate of the second pump can be higher than the flow rate of the first pump. This can assist mixing prior to sampling. Exemplary higher flow rates for the second pump are 550 ul per minute to 2000 ul per minute.

In one embodiment, the pump(s) comprise a stepper motor or a brushless motor comprising an encoder.

Each motor can be controlled by a motor controller, the operation and the sensors of which can be controlled by a microcontroller. The operation of the microcontroller can be controlled by a wireless controller—such as a Bluetooth® controller—to facilitate use with a wireless device—such as a tablet. In a further embodiment, the first pump is located either internally or externally of the cell culture plate. Suitably, the externally located first pump is positioned adjacent the sequentially arranged wells of the cell culture plate. When multiple first pumps are used together with a single cell culture plate, the first pumps may all be located on the same side of the cell culture plate, as exemplified in FIG. 5. In the alternative, due to space constraints, the first pumps may need to be positioned on opposing sides of the cell culture plate, suitably, in a staggered formation, as exemplified in FIG. 2.

The second pump will typically be located externally of the sample plate. Suitably, the externally located second pump is positioned adjacent the cell culture plate so that is can communicate fluid from the cell culture plate to the sample plate. Suitably, the second pump is located on the opposing side of the cell culture plate to the first pump.

An example of a commercially available second pump for use in the present disclosure is the WPM Peristaltic pump (Welco Co, Ltd, Japan) or a Boxer Peristaltic 6KP Series pump (Boxer GmbH, Germany).

In certain embodiments three or more pumps can be used. At least one pump can be used for sampling, at least one pump can be used for refilling of fluid and at least one pump can be used for circulating fluid through the plate (see, for example, FIG. 10).

The at least one pump can be contained in a housing—such as a sealing box. The sealing box can be waterproofed. When more than one pump is used, the pumps can be contained in the same housing or in individual housings, as required.

The at least one pump can be contained in an incubator.

When the at least one pump is contained in a housing, the pump in the housing can be further contained in an incubator. This embodiment is exemplified in FIG. 7 in which each of the motors 56 is contained in a sealing box 56 and housed in an incubator 51.

Cell Culture

Cell culture generally refers to the removal of cells from a tissue prior to growth in an artificial environment. The cells to be cultured can be removed directly from a tissue containing the cell to be cultured and optionally treated with enzymatic or mechanical means prior to culture. As an alternative, the cells to be cultured can be derived from a prior established strain or line of cell. The cell culture plate as described herein can provide a system or device for sampling fluid—such as cell culture medium—from wells. The cell culture plate as described herein can provide a system or device for studying various aspects of a cell including the physiology; the biochemistry; the effects of agents, including aerosols; the screening and development or optimisation of agents; the study of agent efficacy; the study of agent absorption; toxicity screenings; toxicology; target discovery; pharmacokinetics; pharmacodynamics; and regenerative medicine, optionally in real-time.

The cell culture plate can be used in biological end point assays—such as cell based assays that are indicative of overall cell health (for example, CellTiter-Glo® 3D Cell Viability Assay and the ApoTox-Glo® Triplex Assay). It can be used to study cell morphology and phenotype (for example, histology and immunohistochemistry). It can be used to study metabolic capability (for example, the P450-Glo® assays). It can be used to study cell function (for example, the ROS-Glo® $H_2O_2$ Assay or the GSH/GSSG-Glo® Assay).

The cell culture plate can be used to study, for example, toxicology in general, to study the toxicology of agents, to study the toxicology of metabolised agents, and to study the effect of agents on one or more cells.

Inserts and Wells

Certain cells for use in the present disclosure can be cultured in inserts which are housed in the wells of the cell culture plate. Certain cells can be grown on a permeable membrane contained in the insert. In general, the cells will be grown on top of the permeable membrane. The insert is placed in a well of a cell culture plate. When the well of the cell culture plate is filled with fluid—such as cell culture medium—the fluid will pass through the permeable membrane and contact the cells so that they can be cultured in the insert. The fluid may only touch the bottom part of the insert. Different types of cells can be cultured in the insert as described herein. An example of a cell type that is cultured with the use of an insert is a lung cell.

Other cell types for use in the present disclosure can be cultured without the use of an insert and can instead be cultured in wells of the cell culture plate containing a surface coating. For example, spheroids can be grown using Corning® spheroid microplates which have an attachment surface coating, which is hydrophilic, biologically inert and non-degradable, and is covalently attached to the interior surface of the well-bottom. The design of the well-bottom enables highly reproducible growth of 3D cell spheroid cultures. An example of a cell type that is cultured without the use of an insert is a liver cell.

In certain embodiments, the at least two wells are of different depths. For example, when a lung cell and a liver cell are used, the well containing the liver cell will be deeper as fluid needs to cover the lung spheroids, whilst in the well containing the lung cells, the fluid only needs to reach the bottom part of the insert.

In certain embodiments, the fluid level in the at least two wells is of different depths.

FIG. 1 illustrates an embodiment in which an insert 10 comprises a permeable membrane 12 at the base of the insert 10. Tissue/cells 14 can be contained in the insert 10 at the base thereof. The insert can comprise an optional lid 19 on the top of the insert 10 to reduce the risk of contamination. The insert 10 can be contained in a well 17. The well 17 can contain a fluid. Multiple wells 17 can be connected together with a channel—such as a microfluidic channel—as described herein.

The inserts are, advantageously, commercially available which helps to simplify the design and construction of the cell culture plate. By way of example, ThinCert™ permeable cell culture inserts (USA Scientific, Florida, USA) can be used. These are available in various sizes and finishes and can be readily selected by the skilled person for use in the present disclosure. Each insert can have self-positioning hangers that eliminate capillary effects and maximize pipettor access to the well by positioning the insert slightly off-center. ThinCert™ cell culture inserts are compatible with standard multiwell plates. By way of further example, Corning® HTS Transwell®-permeable supports (Sigma Aldrich, Dorset, United Kingdom) can be used. Corning® HTS Transwell®-permeable supports have an array of 24 or 96 wells with permeable inserts connected by a rigid tray.

Discontinuous Surface

It has been observed by the present inventors that spheroids can have a tendency to agglomerate together in the same place during 3-dimensional cell culture to form a single large tissue. Without wishing to be bound by theory, they have observed that cells in the middle of a spheroid have less access to nutrients compared to cells located towards the outside of the spheroid, such that cells towards the middle of the spheroid have a tendency to die. This becomes problematic when spheroids agglomerate (which can occur after 5 hours of cell culture) because a higher number of cells in the spheroid will have less access to nutrients. This also further increases the number of dead cells within the spheroid. This can be problematic for a number of reasons, including: (1) molecules released from the dead cells can have a negative impact on other cells in the spheroid; (2) dead cells are not metabolically active, so the metabolic activity of the spheroid will be reduced; and (3) many assays require the use of a single spheroid. The present inventors' sought to solve the problem of spheroids agglomerating in 3-dimensional cell culture. They surprisingly discovered that this problem could be elegantly solved by forming a discontinuous surface on the base of a well—such as a well of a multi-well plate—such that spheroids on the discontinuous surface become trapped in the discontinuous surface. This effectively reduces the extent of or prevents the agglomeration of the spheroids. Advantageously, the inventors' discovered that spheroids can be maintained as individualised single spheroids.

In certain embodiments, the base of the one or more wells—such as the base of one or more wells of a multiwell plate—can comprise a discontinuous surface adapted to reduce or prevent the agglomeration of spheroids. It is to be understood that not every well needs to include the discontinuous surface as not all wells may be used for the culture of spheroids. For example, some wells may be used for the culture of other cell types, which do not require the use of the discontinuous surface. For example, some wells may be used for the culture of other cell types, which require the use of an insert to create an air-liquid interface.

Suitably, the discontinuous surface traps the spheroids to reduce or prevent the agglomeration thereof. Suitably, the discontinuous surface traps single spheroids to reduce or prevent the agglomeration thereof.

In certain embodiments, the discontinuous surface is formed by one or more grooves. The grooves can function to trap the spheroids to reduce or prevent the agglomeration thereof. The size of the groove(s) will generally correspond to the largest diameter±10% of a spheroid so that the spheroids can be trapped or held in the groove(s). Suitably, the groove(s) will cover the majority of the base of the well as the presence of a flat surface on the base of the well can lead to the spheroids agglomerating, which can lead to the formation of large cell aggregates which is not desirable. In certain embodiments, at least 70%, 80%, 90%, 95%, 99% or 100% of the base of the well will contain the discontinuous surface—such as the groove(s).

Suitably, the depth and width of the discontinuous surface—such as the plurality of grooves—in the base of the well is between about 200 µm to about 1000 µm, suitably, between about 600 µm to about 1000 µm. The actual depth and width will be determined by the size of the spheroids which are intended to be used in the well and trapped. So, for example, some spheroids have a maximum diameter of about 600 µm, in which case the depth and width of the discontinuous surface—such as the plurality of grooves—will be about 600 µm±10%. In some embodiments, it is desirable for the depth and width of the discontinuous surface—such as the plurality of grooves—to be greater than the maximum diameter of the spheroid—such as 20%, 30%, 40%, 50% or 60% or more greater than the maximum diameter of the spheroid. In one embodiment, the spheroid has a maximum diameter of 600 µm and the discontinuous surface—such as the plurality of grooves has a height of about 1 mm and a width of about 1 mm or a width of about 2 mm.

Generally, the shape of the grooves can be a flat shaped bottom, a U-shape, a V-shape, or a V-shape with a flat bottom and the like. In one embodiment, the grooves have a V-shape with a flat bottom. In one embodiment, the maximum width of the opening of the groove is about 2.4 mm, the depth of the groove is about 1 mm and the width of the flat bottom on the base of the groove is about 400 µm. The angle of the opposing sides of the groove according to this embodiment is about 90 degrees.

Figure 11:
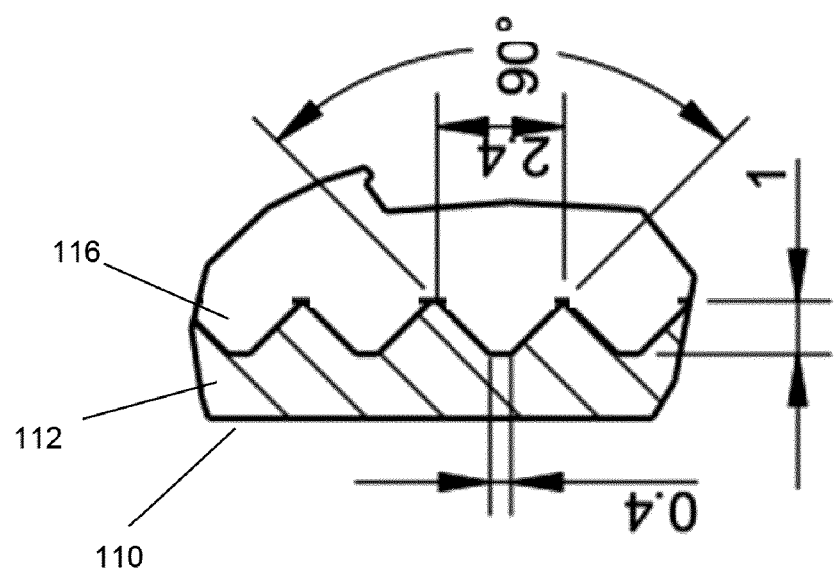
FIG. 11 is a cross-section of the well with a plurality of concentric grooves for trapping individual spheroids (marked as 'voir detail B' in FIG. 14). Dimensions are in millimetres.

Turning to FIG. 11, there is shown a cell culture plate 110 comprising a well 112 with a plurality of grooves 116 on the base thereof containing V-shaped grooves each with a flat bottom. The maximum width of the opening in the grooves is about 2.4 mm, the depth of the grooves is about 1 mm and the width of the flat bottom on the base of the grooves is about 400 µm. The angle of the opposing sides of the grooves is about 90 degrees. Although the plurality of grooves are illustrated as having the same shape it is contemplated that grooves with different shapes can be used. For example, the base of the well may comprise a plurality of grooves in which the shape of one or more of the grooves is different. The base of the well may therefore comprise a plurality of grooves containing two or more of a flat shaped bottom, a U-shape, a V-shape, or a V-shape with a flat bottom and the like.

Figure 12:
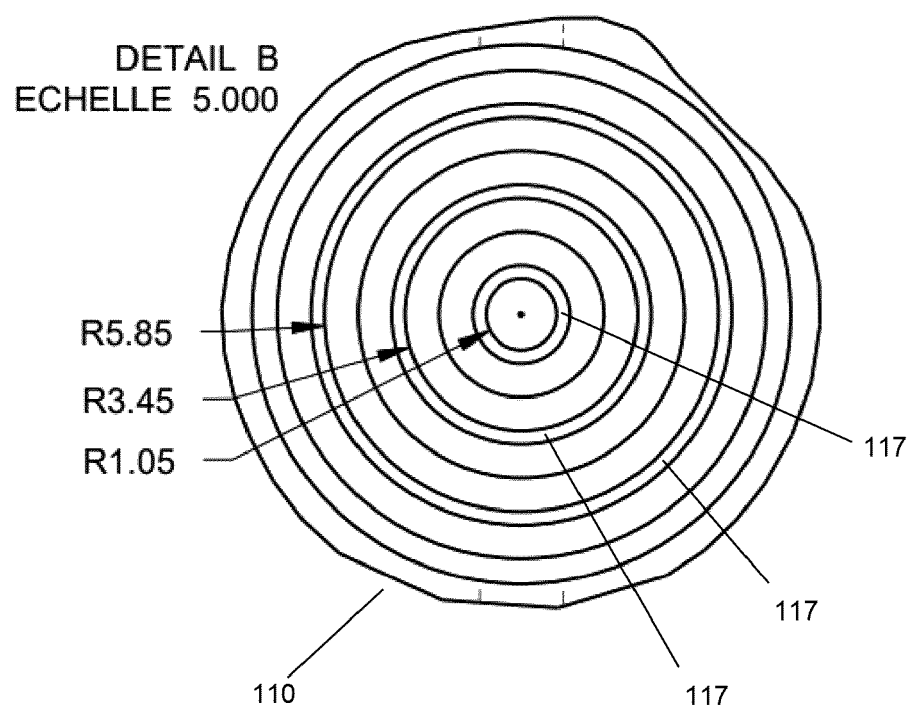
FIG. 12 is a plan view of the well with a plurality of concentric grooves for trapping individual spheroids (marked as 'voir detail B' in FIG. 14). Dimensions are in millimetres.
Figure 13:
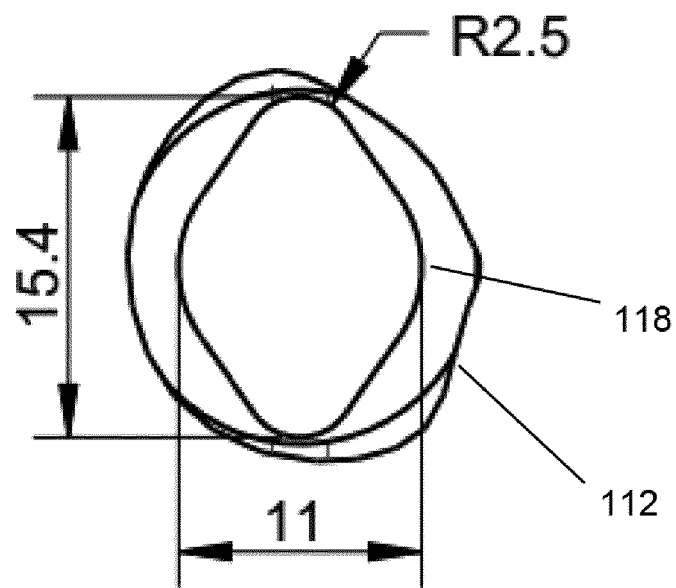
FIG. 13 is a plan view of the well containing a microfluidic channel (marked as 'voir detail C' in FIG. 4). Dimensions are in millimetres.

In certain embodiments, the grooves form a plurality of concentric rings on the base of the well. In one embodiment, the radius of the concentric rings is about 1.05 mm, about 3.45 and about 5.85 mm. Turning to FIG. 12, there is shown the base of a cell culture plate 112 with a plurality of concentric rings 117 formed by the grooves 116, the radius of the concentric rings being about 1.05 mm, about 3.45 and about 5.85 mm.

Figure 14:
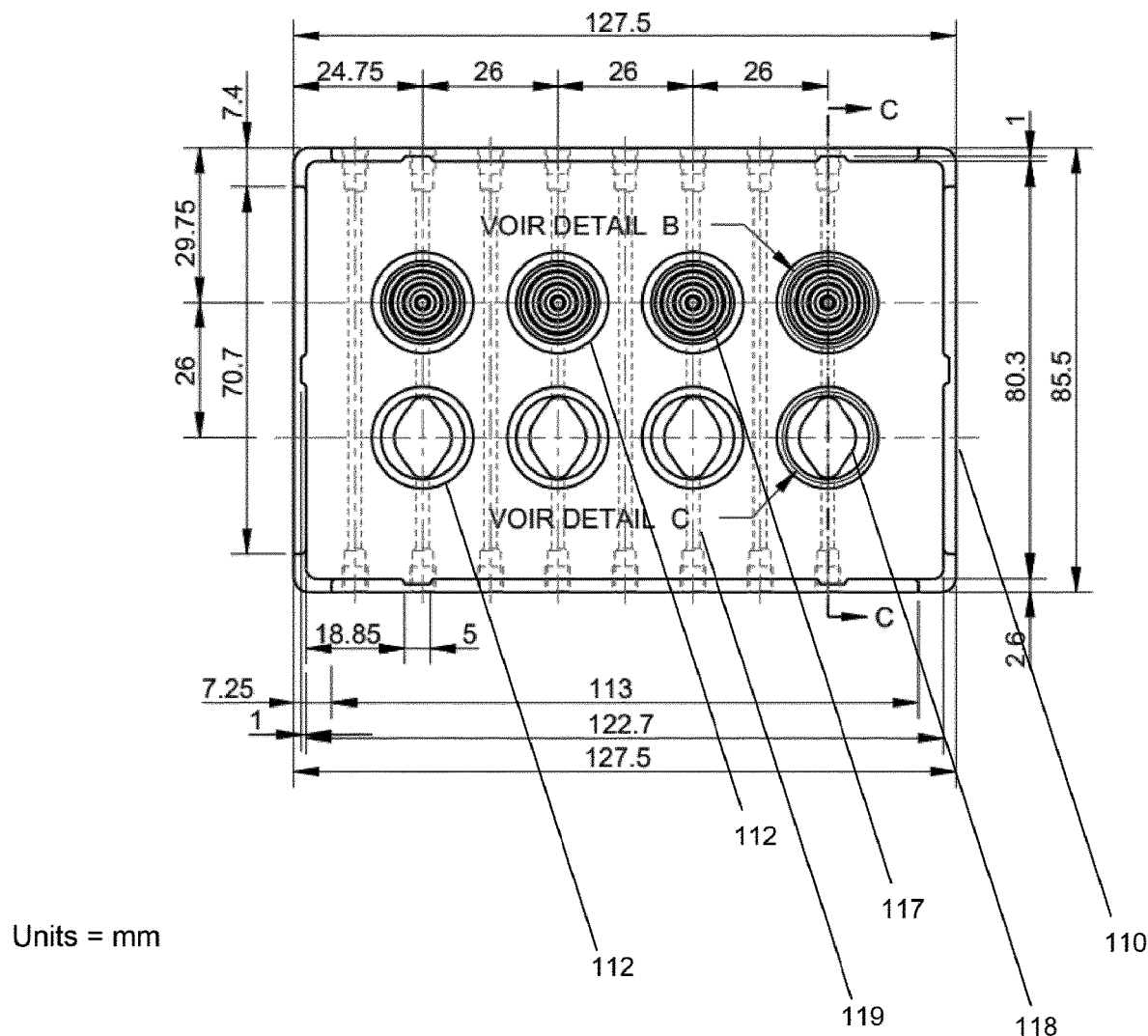
FIG. 14 is a plan view of a multi-well plate containing wells with a plurality of concentric grooves for trapping individual spheroids (marked as 'voir detail B') and wells containing an insert (marked as 'voir detail C'). The wells are connected by a channel such that each of the first well ('voir detail B') and the second well ('voir detail C') are in fluid communication with each other. Dimensions are in millimetres.

Turning now to FIG. 14, there is shown a plan view of a cell culture plate 110 in the form of a multi-well plate. The cell culture plate 110 contains a plurality of wells 112, the wells containing either a plurality of concentric grooves 117 or containing a microfluidic channel 118. The wells are arranged linearly in rows. A row can be configured to contain at least one well containing the concentric grooves 117. A row can be configured to contain at least one well containing the concentric grooves 117 and at least one well containing a microfluidic channel 118, as shown in FIG. 4.

A channel 119 connects a well containing a plurality of concentric grooves 117 and a well containing a microfluidic channel 118. Each well contains an inlet and an outlet for fluid communication into each well and out of each well. Although FIG. 14 shows every cell well 112 in the cell culture plate 110 containing either the concentric grooves 117 or containing the microfluidic channel 118, the skilled person will understand that it is not essential for every well 112 to be configured in this way and that is possible for one or more of the wells 12 to not contain the concentric grooves 117 and/or to not contain the microfluidic channel 118. Some of the wells 112 can be empty and not used, as required.

In certain embodiments, the discontinuous surface is formed by one or more grooves that are shaped as waves across the base of the well.

In certain embodiments, the discontinuous surface comprises a plurality of holes. The holes will typically have a closed bottom and an open top. The holes function to trap individual spheroids to reduce or prevent the agglomeration thereof. The size of the holes will generally correspond to the largest diameter±10% of a spheroid so that the spheroids can be trapped or held in the holes. The discontinuous surface may contain 10, 20, 30, 40, 50, 60, 70, 80, 90, 100, 110, 120, 130, 140, 150, 160, 170, 180, 190 or 200 or more holes distributed across the bottom of the well. The discontinuous surface may contain from 130 to 160 holes distributed across the bottom of the well. The discontinuous surface may contain from 130 to 150 holes distributed across the bottom of the well. The discontinuous surface may contain from 130 to 140 holes distributed across the bottom of the well. Generally, the shape of the holes can include a flat shaped bottom, a U-shape, a V-shape, or a V-shape with a flat bottom and the like. The shape of the holes is not particularly limited provided that the holes are able to accommodate the largest diameter±10% of a spheroid in order to trap individual spheroids. In certain embodiments, the depth and width of the holes is between about 200 to about 1000 um, suitably, between about 600 to about 1000 µm. In certain embodiments, at least 70%, 80% or 90% or more of the base of the well will be populated with holes.

Figure 16:
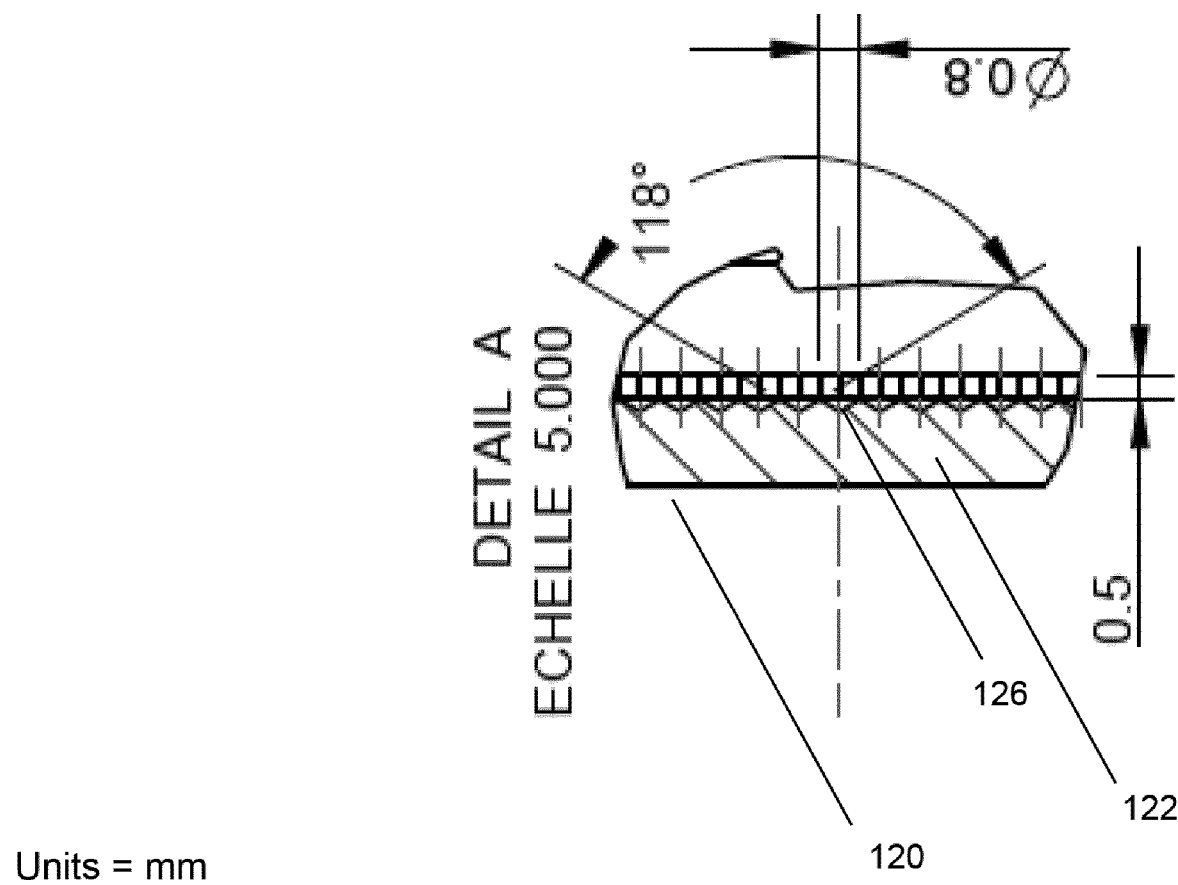
FIG. 16 is a cross-section of the well with a plurality of holes to achieve the function of trapping individual spheroids (marked as 'voir detail B' in FIG. 15).

Turning to FIG. 16, there is shown a cell culture plate 120 comprising a well 122 with a plurality of holes 126 on the base thereof. The holes have a closed bottom and an open top. The maximum width of each hole is about 0.8 mm, the depth of the grooves is about 0.5 mm. The angle of the opposing sides of the holes is about 118 degrees. Although the plurality of holes are illustrated as having the same shape it is contemplated that holes with different shapes can be used. For example, the base of the well may comprise a plurality of holes in which the shape of one or more of the holes is different. The base of the well may therefore comprise a plurality of holes containing two or more of a flat shaped bottom, a U-shape, a V-shape, or a V-shape with a flat bottom and the like.

Figure 17:
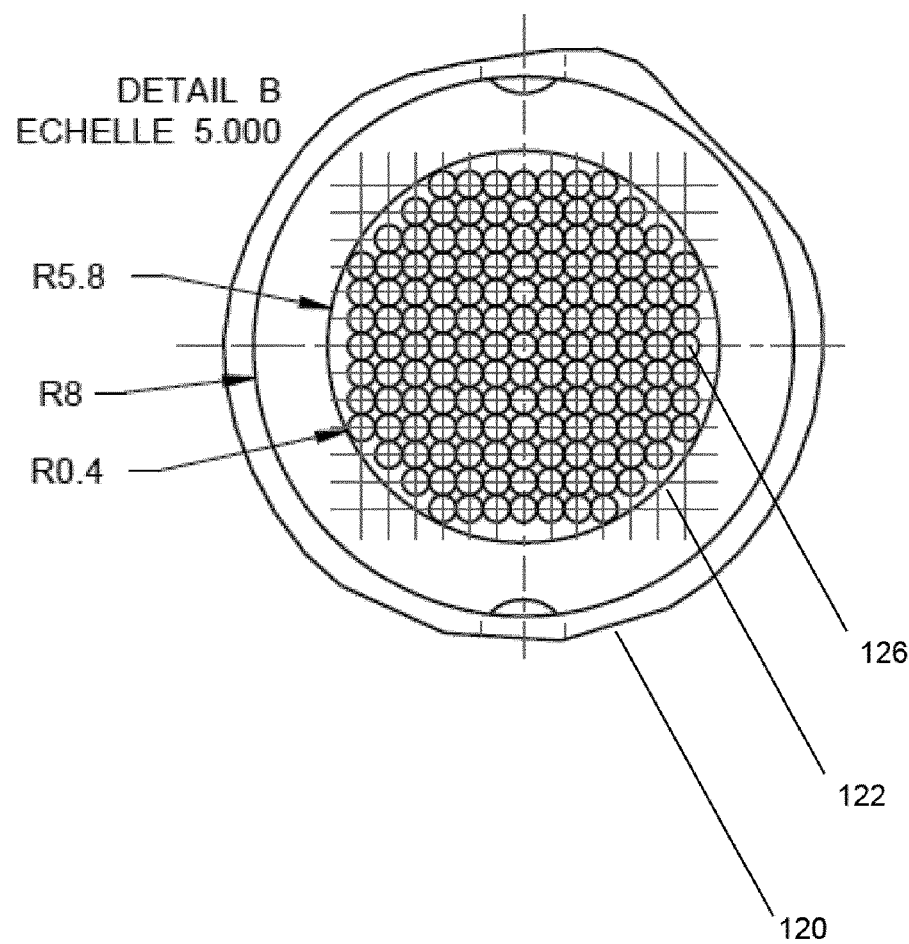
FIG. 17 is a plan view of an individual well with a plurality of holes for trapping individual spheroids, as shown in FIG. 16. Dimensions are in millimetres.

FIG. 17 illustrates a plan view of the cell culture plate 120 shown in FIG. 16. The radius of the cell culture plate 120 is about 8 mm. The radius of the base of the well 122 containing the plurality of holes 126 is about 5.8 mm. The radius of each hole 26 is about 0.4 mm.

Figure 18:
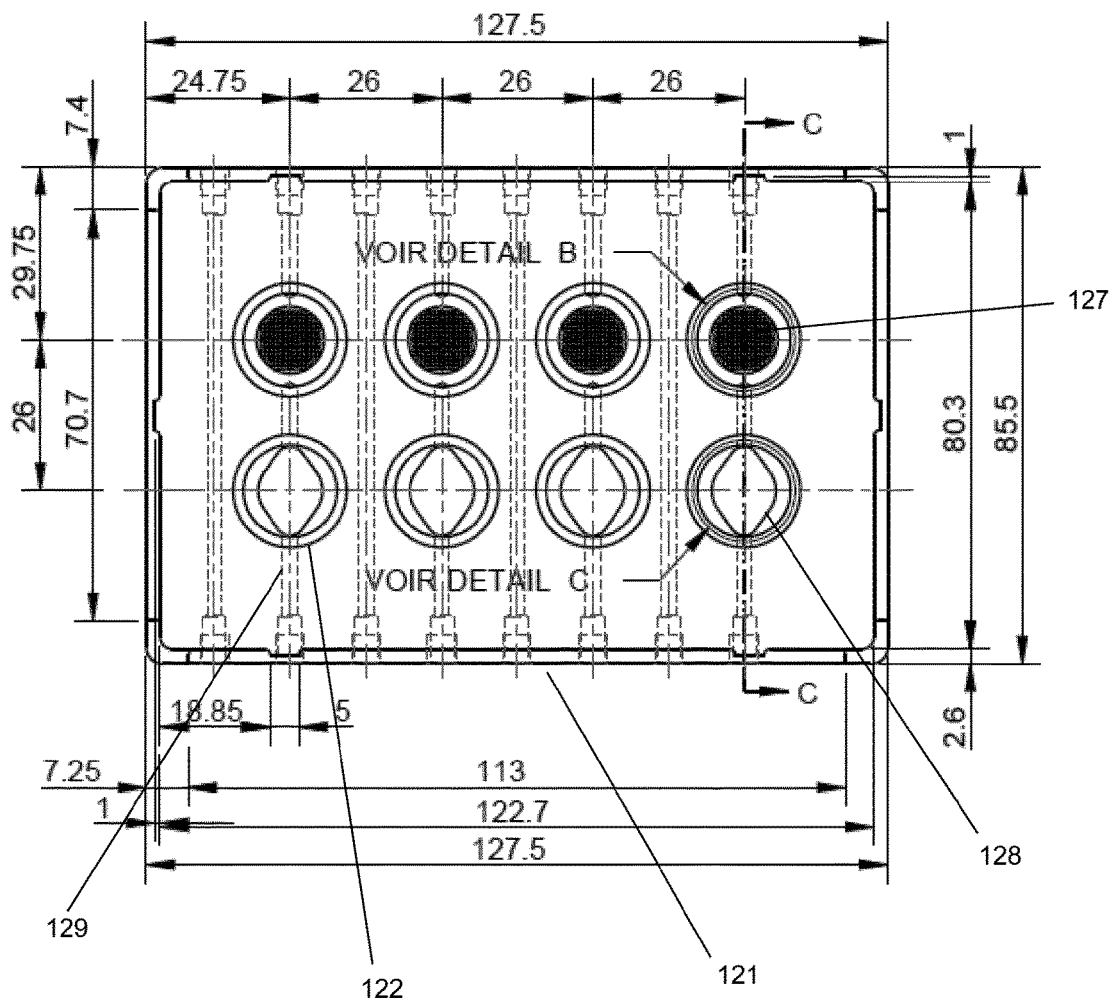
FIG. 18 is a plan view of a multi-well plate containing wells with a plurality of holes for trapping individual spheroids (marked as 'voir detail B') and wells containing an insert (marked as 'voir detail C'). The wells are connected by a channel such that each of the first well ('voir detail B') and the second well ('voir detail C') are in fluid communication with each other. Dimensions are in millimetres.

Turning now to FIG. 18, there is shown a plan view of a cell culture plate 121 in the form of a multi-well plate. The cell culture plate 121 contains a plurality of wells 122, the wells containing either a plurality of holes 127 or containing a microfluidic channel 128. The wells 122 are arranged linearly in rows. A row can be configured to contain at least one well containing the plurality of holes 127. A row can be configured to contain at least one well containing the plurality of holes 127 and at least one well containing a microfluidic channel 128, as shown in FIG. 14. A channel 129 connects a well containing a plurality of holes 127 and a well containing a microfluidic channel 128. Each well contains an inlet and an outlet for fluid communication into each well and out of each well.

Although FIG. 18 shows every well 122 in the cell culture plate 121 containing either the holes 127 or containing the microfluidic channel 128, the skilled person will understand that it is not essential for every well 122 to be configured in this way and that is possible for one or more of the wells 122 to not contain the holes 127 and/or to not contain the microfluidic channel 128. Some of the wells 122 can be empty and not used, as required.

The depth of a plurality of wells, when used in accordance with the present disclosure, does not need to be the same across the cell culture plate and it is contemplated that the wells can have different depths. In one embodiment, the well comprising the discontinuous surface or the holes has a depth that is greater than the well comprising the insert. The channel connecting the at least two wells can be at the same height such that the channel is located at different distances from the base of the at least two cell wells. This configuration ensures that the flow of fluid into the well does not perturb or disturb the spheroids trapped on the discontinuous surface, whilst ensuring that the fluid can still pass through the permeable membrane of the insert.

Figure 15:
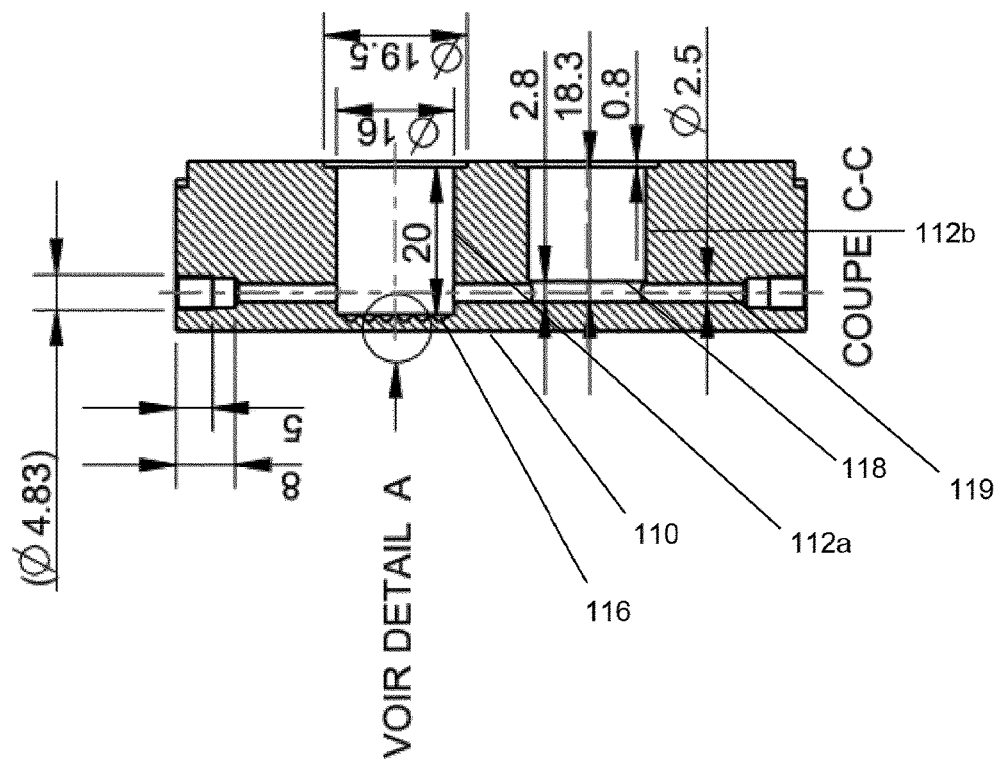
FIG. 15 is a cross sectional view of line C-C in FIG. 14.

This configuration is depicted in FIG. 15, where there is shown a cell culture plate 110 comprising a first well 112*a* with a plurality of grooves 116 on the base thereof and a second well 112*b* with a microfluidic channel 118 therein. The first well 112*a* has a depth that is greater than the second well 112*b*. The first well 112*a* has a depth of about 20 mm and the second cell well 112*b* has a depth of about 18.3 mm. The channel 119 is in fluid communication with each of the wells 112*a* and 112*b*. The channel 119 is located further from the base of the first well 112*a* as compared to the second well 112*b*.

Figure 19:
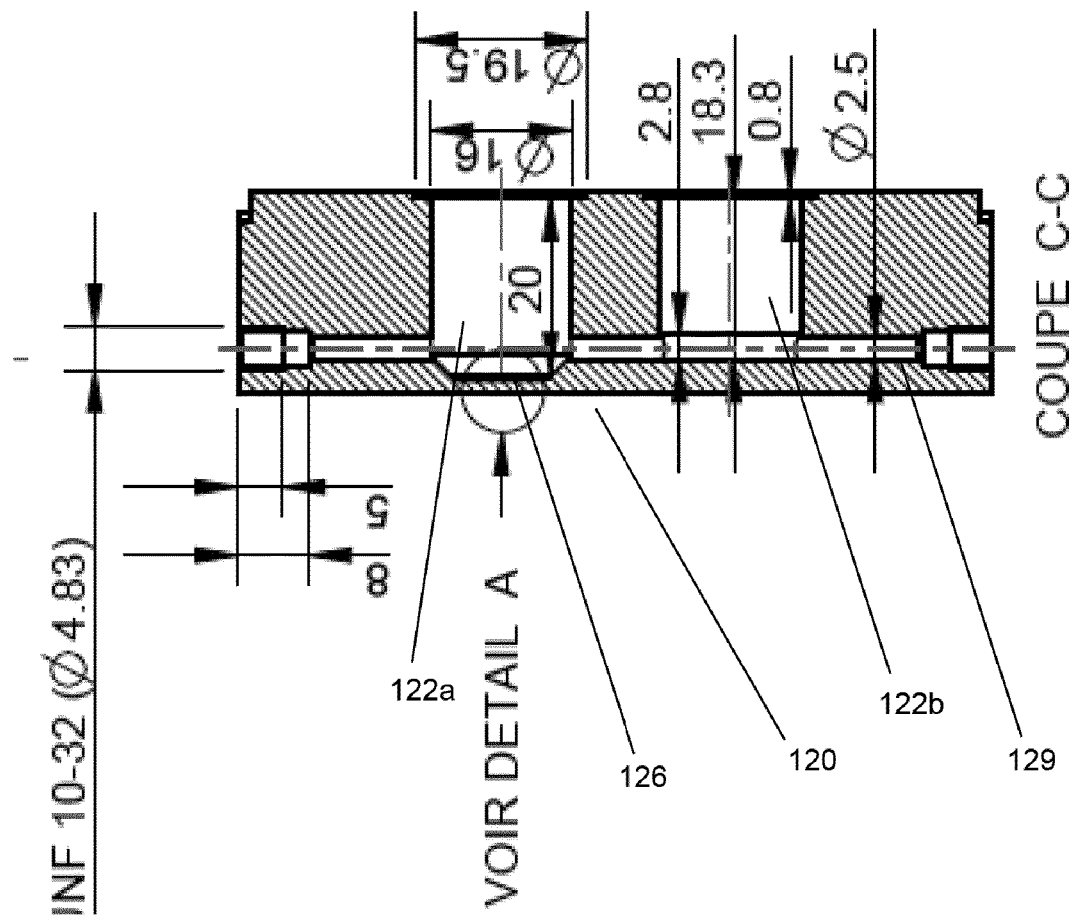
FIG. 19 is a cross sectional view of line C-C in FIG. 18.
Figure 20:
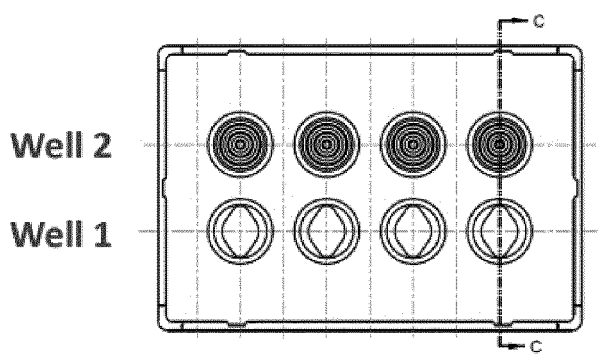
FIG. 20 shows the results of the shear stress calculated for each of the two different wells as shown in the Figure and the parameters used to calculate the shear stress.

This configuration is also depicted in FIG. 19, where there is shown a cell culture plate 120 comprising a first well 122*a* with a plurality of holes 126 on the base thereof and a second well 122*b* with a microfluidic channel 128 therein. The first well 122*a* has a depth that is greater than the second well 122*b*. The first well 122*a* has a depth of about 20 mm and the second well 112*b* has a depth of about 18.3 mm. The channel 129 is in fluid communication with each of the wells 122*a* and 122*b*. The channel 129 is located further from the base of the first well 122*a* as compared to the second well 122*b*.

Cell Sources

The present disclosure utilises various sources of cells. In one embodiment, the present disclosure excludes the step of isolating or obtaining a cell sample from a subject. The cells can be cryopreserved. The cells can be in three dimensional culture. The cells can be in the form of spheroids. The cells can be actively dividing. The cells can be cultured in cell culture medium (for example, comprising nutrients (for example, proteins, peptides, amino acids), energy (for example, carbohydrates), essential metals and minerals (for example, calcium, magnesium, iron, phosphates, sulphates), buffering agents (for example, phosphates, acetates), indicators for pH change (for example, phenol red, bromo-cresol purple), selective agents (for example, chemicals, antimicrobial agents), etc.). A single cell culture medium can be used to grow cells of the same or different types. Different cell culture media can be used to grow different types of cells. Since the cell culture media is circulated in accordance with the present disclosure then mixing of the different cell culture media will occur.

In some embodiments, one or more agents are included in the cell culture medium or cell culture media. Cells can be isolated from a tissue or a fluid using methods that are well known in the art. Cells can be differentiated from stem cells—such as embryonic stem cells or induced pluripotent stem cells, or directly differentiated from somatic cells. The cells may be natural cells or altered cells (for example, a cell comprising one or more non-natural genetic alterations). The cell may be a disease cell or disease model cell. For example, the cell can be a cancer cell or a cell that can be induced into a hyper-proliferative state (e.g., transformed cells).

Cells may be or may be derived from human or animal subjects or from human or animal cells, including any of a number of mammalian species, suitably human, but including rat, mouse, pig, rabbit, and non-human primates and the like. Cells and cell lines can be obtained from commercial sources. Cells may be from or derived from any desired tissue or organ type, including but not limited to, adrenal, bladder, blood vessel, bone, bone marrow, brain, cartilage, cervical, corneal, endometrial, oesophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid.

Lung cells—including lung epithelial cells—are one cell type of particular interest. Bronchial and/or airway epithelial cells are of particular use in the present disclosure. Human bronchial epithelial cells can be collected by brushing donor lungs during a bronchoscopy procedure. In one embodiment, the lung cells are Normal Human Bronchial Epithelial (NHBE) cells. The lung epithelial cells can be cultured as a monolayer of undifferentiated cells or further developed into an organotypic lung epithelium-like tissue at an air-liquid interface. Lung epithelial cells can be obtained from human or animal subjects with different pathologies, including subjects that are classified as smokers or non-smokers.

Liver cells are another cell type of particular interest. In one embodiment, the cells used are hepatocytes. Hepatocytes are cells of the liver, which make up 70-85% of the liver's cytoplasmic mass. The functionality of hepatocytes is highly dependent on their capacity to form a polar phenotype, which is only established in 3-dimensional culture. One source of liver cells is primary hepatocytes which are an in vitro model widely used to investigate numerous aspects of liver physiology and pathology. The technique used to isolate human hepatocytes can be based on a two-step collagenase perfusion of a donated liver. However, these cells do not express metabolic enzymes for more than 5 days. Another limitation is their short viability. These drawbacks can be overcome by the use of alternative, long-lived liver cell lines—such as human or animal hepatic progenitor cell lines. One such example of a human hepatic progenitor cell line is the HepaRG cell line (ThermoFisher Scientific). HepaRG cells retain many characteristics of primary human hepatocytes. They have greater liver-specific and metabolic gene expression compared to primary hepatocytes and a longer lifespan. Reorganisation of HepaRG cells in 3-dimensional spheroids further increases both the lifespan and metabolic capabilities, suggesting that spheroids may provide a better alternative in vitro liver model for toxicity testing. Liver spheroids can also be created with a mixture of primary hepatocytes and liver stellate cells or primary hepatocytes and adipose tissue-derived stem cells.

In one embodiment, the lung cell is a lung epithelial cell—such as a bronchial and/or airway epithelial cell.

In one embodiment, the liver cell is a HepaRG cell, suitably, a spheroid HepaRG cell.

Combinations of Cells

The use of combinations of any of the cells described herein is contemplated. The use of combinations of any of the cells described herein in the cell culture plate or in a system or device comprising the cell culture plate is contemplated. One exemplary combination of cells is the combination of liver and lung cells. The combination of a lung epithelial cell—such as a bronchial and/or airway epithelial cell, and a liver cell—such as a HepaRG cell, suitably, a spheroid HepaRG cell is contemplated. Additional cells can be used together with this combination if required.

The different cells of the combination will generally be cultured in separate wells.

In the cell culture plate comprising at least two wells or at least two inserts, each of the wells or inserts can contain the same or a different cell type. Suitably, each of the at least two wells or inserts contain a different cell type. The different cell type may be a different cell line. The different cell type may be a different cell or tissue. In one exemplary embodiment, the different cell types in the cell culture plate are lung and liver cells.

One advantage of the present disclosure is that the impact of a first cell type on a second cell type can be studied, optionally in real time, as fluid from the first cell type reaches the second cell type as it is circulated through the cell culture plate described herein.

Another advantage of the present disclosure is that the impact of a second cell type on a first cell type can be studied, optionally in real time, as fluid from the second cell type reaches the first cell type as it is circulated through the cell culture plate described herein.

Another advantage of the present disclosure is that the impact of a metabolized agent from a first cell type on a second cell type can be studied, optionally in real time.

Another advantage of the present disclosure is that the impact of a metabolized agent from a second cell type on a first cell type can be studied, optionally in real time.

Another advantage of the present disclosure is that the impact of a metabolized agent from a first cell type and a metabolized agent from a second cell type on a third cell type can be studied and so on, optionally in real time.

Another advantage of the present disclosure is that the impact of a metabolized agent from combinations of cell types can be studied, optionally in real time.

Another advantage of the present disclosure is that the impact of the exposure of two or more cell types to an agent can be studied, optionally in real time.

3-Dimensional Cell Culture

The present disclosure incorporates the use of "3-dimensional cell culture", which includes any method that provides for the culture of a cell in 3 dimensions, with or without the use of a matrix or scaffold—such as the permeable membrane in the insert. A number of different 3-dimensional cell culture methods have been developed including, spheroid cultures and organotypic cultures. 3-dimensional cells can be grown and/or maintained in the cell culture plate described herein.

The term "spheroid" assumes the meaning as normally understood in the art which is either a single cell that divides into a ball of cells in 3-dimensions, or an aggregation of multiple cells in 3-dimensions, either with or without the use of a matrix or scaffold to support in 3-dimensional cell growth within the spheroid. The 3-dimensional spheroid can be an adherent spheroid or a spheroid grown in suspension.

In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown.

3-dimensional spheroids more closely resemble in vivo tissue in terms of their cellular communication and development of extracellular matrices. These matrices assist the cells in moving within the spheroid similar to the way cells would move in living tissue. The spheroids are thus much improved models for differentiation, survival, cell migration, cell polarisation, gene expression and growth.

Spheroids can be harvested and studied using various methods well known in the art, including colorimetric, fluorescence, and luminescence assays measured with a plate reader or they can be readily observed by microscopy. Additional techniques include western, northern or southern blot, histological techniques (for example, immunohistrochemistry, in situ hybridization, immunoflourescence) and the like. The use of optical imaging methods—such as inverse bright field microscopy, fluorescence microscopy, single-photon emission computed tomography (SPECT), positron emission topography (PET), magnetic resonance imaging (MRI) and Cerenkov luminescence imaging (CLI) techniques is also contemplated. Applications of the use of 3-dimensional spheroids include the study of the proliferation of cells and tissues in vitro in an environment that more closely approximates that found in vivo, the screening of compounds or agents, toxicology assays, cell therapy, cell delivery, agent delivery, biochemical replacement, production of biologically active molecules, tissue engineering, biomaterial, and clinical trials and the like.

The use of spheroids in 3-dimensional cell culture is generally reviewed in *Expert Opin. Drug Discov.* (2015) 10, 519-540.

3-dimensional organ culture systems can be used in the present disclosure and they allow the study of how organs function. Response to certain stimuli, response to one or more agents, and pharmacokinetic behaviour of such agents can be studied. Miniaturised 3-dimensional cell culture systems allow the combined study of groups of cells or organs. This allows the complexity of interaction between different tissues to be reproduced. The 3-dimensional organ culture can be organotypic, which means that it seeks to reproduce major functions of an organ or organ system. A miniaturised fluidic system interconnecting the wells is also contemplated.

The cell culture plate can have at least one physiological function of at least one tissue type, or more suitably has at least one physiological function of at least two different tissue types.

Liver Based 3-Dimensional Cultures

The liver plays a central role in detoxification, metabolism of carbohydrates, lipids and proteins as well as biotransformation of endogenous and exogenous substances. Liver functionality is closely linked to the assembly of highly specialised cells, the majority of which are hepatocytes, embedded in a complex 3-dimensional structure made up of so-called lobules. Biotransformation of compounds usually results in non-toxic and more soluble metabolites, however, occasionally, more toxic metabolites may be formed causing hepatotoxicity.

Hepatocytes can be changed into 3-dimensions via various methods, including the use of sandwich culture, solid scaffold materials—such as polystyrene scaffolds, hydrogels—such as collagen type-I, or self-assembling of hepatocytes into spheroids.

Whilst the use of freshly isolated primary human hepatocytes limited may be the preferred lung cell type, their availability is limited. Other choices of human liver cell lines include HepG2 and Hep2/C3A. A particularly suitable cell source is the HepaRG cell line. Other sources of human hepatocytes are human embryonic stem cell (hESC) derived hepatocytes and hepatocytes derived from induced pluripotent stem cells (iPSC).

In one embodiment, the spheroid is or is derived from a liver cell to form a 3-dimensional liver spheroid. Such liver spheroids can be prepared using various methods that are known in the art and described in, for example, *ALTEX* (2014) 31, 441-477 and *Toxicol. Sci. Off. J. Soc. Toxicol.* (2013) 133, 67-78.

Lung Based 3-Dimensional Cultures

As the morphology of the respiratory tract changes from the upper to the lower airways, many different cell culture models have been established using primary cells or cell lines and are contemplated for use in the present disclosure. The choice of exactly which cell or cell line to use will depend on the area of interest of the respiratory tract for a given study.

Since the lung surface is exposed to air, the cell model can be cultured at the air-liquid interface to mimic the lung more realistically.

In one embodiment, the spheroid is or is derived from a lung cell to form a 3-dimensional lung spheroid. Such lung spheroids can be prepared using various methods that are known in the art, such as those described in *ALTEX* (2014) 31, 441-477 and *Toxicol. Sci. Off. J. Soc. Toxicol.* (2013) 133, 67-78.

Cell Fluid Exposure Sampling Device

The cell culture plate can be a component of a larger device—such as a sampling device, suitably, a cell fluid exposure sampling device. Fluid that is in contact with cells from at least two wells can be circulated through the device or system and sampled and optionally measured and/or analysed, as required. To deliver samples of fluid from the cell culture plate to the sample plate, a second (sampling) pump can be used to communicate fluid from the cell culture plate to the sample plate. The second pump is described above. In general, the device can contain three or more pumps. At least one pump can be used for sampling, at least one pump can be used for refilling of fluid and at least one pump can be used for circulating fluid through the plate (see, for example, FIG. 10). Advantageously, the sampling device is an automated sampling device which minimizes manual interaction to enhance throughput and reduce the risk of contamination. In certain embodiments, the sampling device is a high-throughput sampling device. In certain embodiments, the sampling device is configured for real-time sampling. In certain embodiments, the sampling device is configured for high-throughput sampling in real-time.

In some embodiments, the sampling device comprises a plurality (for example, 2, 3, 4, 5, 6, 7, 8, 9 or 10 or more) of cell culture plates and a plurality (for example, 2, 3, 4, 5, 6, 7, 8, 9 or 10 or more) of sample plates.

In some embodiments, the sampling device comprises an incubator for housing the cell culture plate to maintain it at optimal culture conditions (for example, temperature, atmosphere and humidity).

In some embodiments, the sampling device is housed inside an incubator.

In some embodiments, the sampling device comprises one or more pumps or other components for supplying or re-supplying fluid to the cell culture plate(s).

In some embodiments, the sampling device comprises one or more robotic components (for example, pipettes, arms, plate movers and the like) for automating the handing, use, and/or analysis of culture devices.

In some embodiments, the sampling device comprises one or more reservoirs to supply or replenish (fresh or unused) fluid to the sampling device.

In some embodiments, the sampling device comprises one or more cleaning reservoirs to supply cleaning fluid to the device.

The sampling device can be completely or partially automated.

Figure 8:
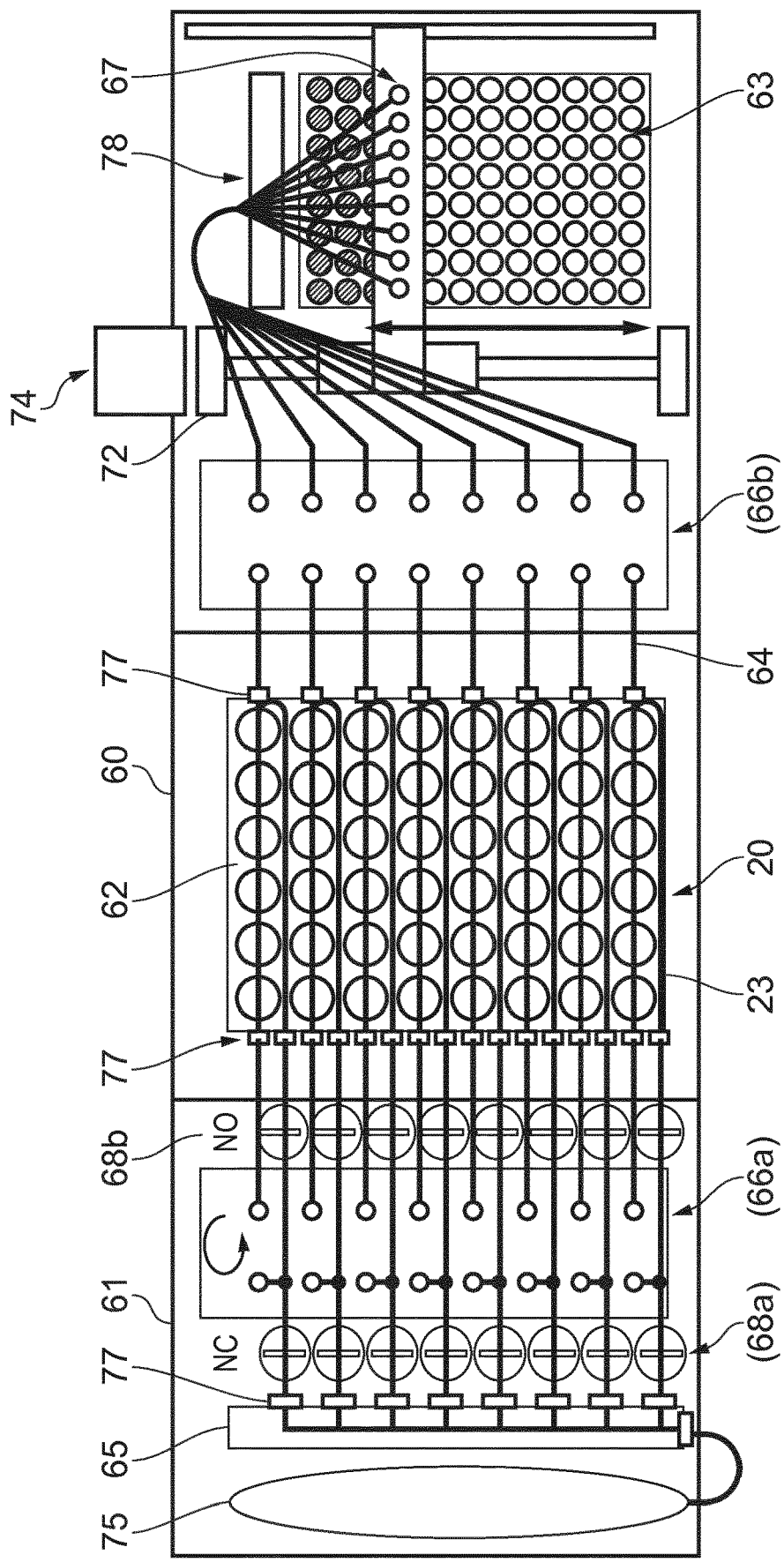
FIG. 8 illustrates a sampling device that incorporates the cell culture plate of the present disclosure.

The sampling device comprises the cell culture plate described herein. To allow fluid communication between the cell culture plate and the sample plate, a second pump can be used to communicate fluid from the cell culture plate towards the sample plate. The second pump can communicate with the cell culture plate by adapting the channel to additionally extend to the second pump. Alternatively, a second channel can be connected to or coupled to the (first) channel in the cell culture plate, as shown in FIG. 8 by reference numeral 64.

The second channel can be connected or coupled to the second pump which is operable to communicate fluid away from the wells in the cell culture plate and towards the sample plate. The sampling device can further include a reservoir for storing fluid in the device, wherein said reservoir is in fluid communication with the wells.

In certain embodiments, it can further comprise at least one further pump adapted to communicate fluid from the reservoir to refill the wells of the cell culture plate and/or the sample collection plate. In certain embodiments, the at least one further pump is adapted to refill the wells of the cell culture plate with the same volume of fluid as collected in the wells of the sample collection plate. In certain embodiments, it further comprises a pipettor adapted to transfer fluid into the wells of the sample collection plate. One or more samples at one or more different times points for the sequentially arranged wells in the cell culture plate can be sampled for analysis.

In certain embodiments, the sampling device can comprise a computer controller operable to automatically control the operation of the device. In certain embodiments, it can comprise a means to detect fluid levels in the device.

Figure 10:
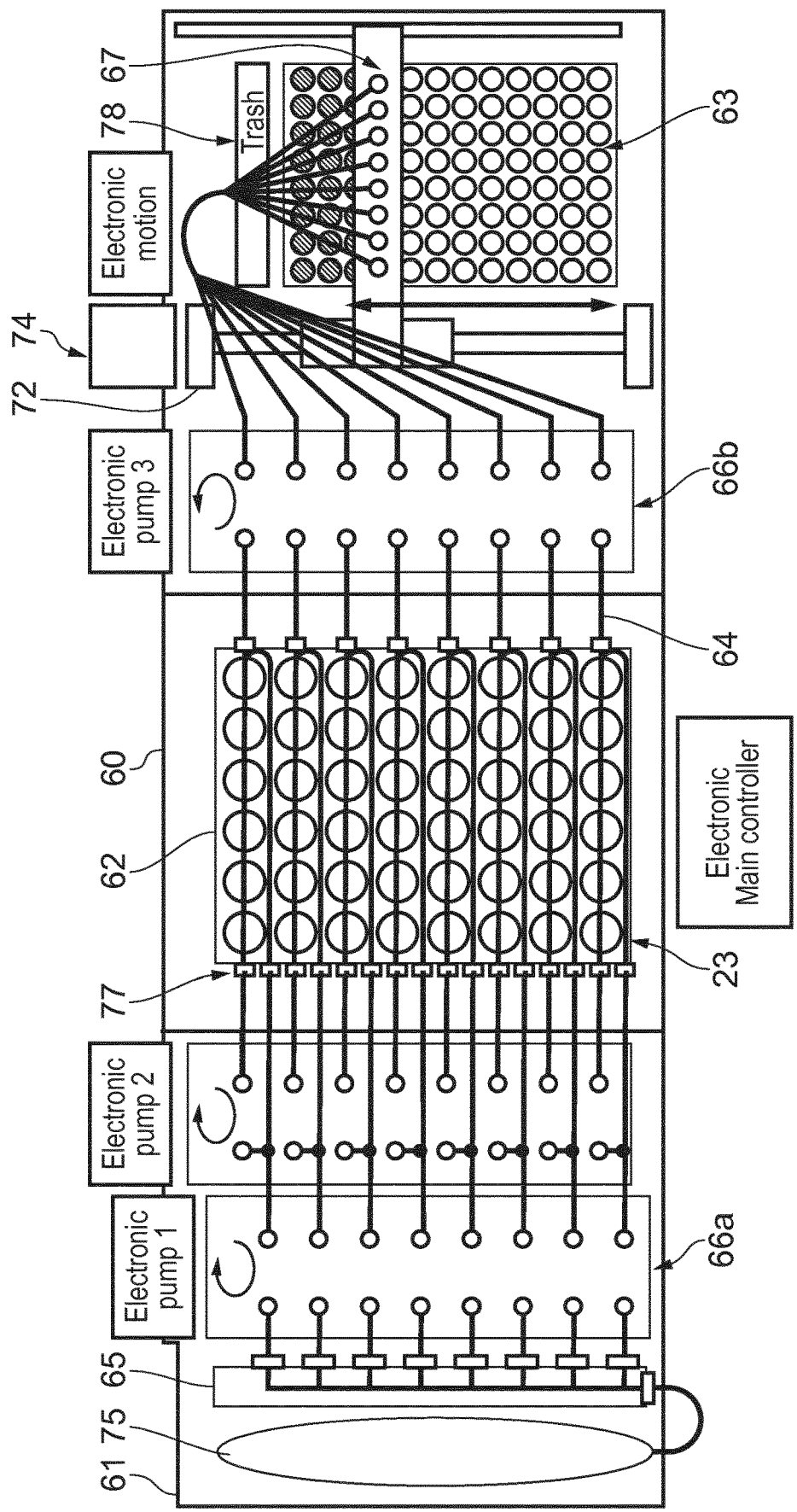
FIG. 10 illustrates a further embodiment of a sampling device of the present disclosure that incorporates a cell culture plate and three pumps.

A specific non-limiting example of a sampling device that can incorporate a cell culture plate and a sample plate is now described in more detail. FIG. 8 illustrates a cell fluid exposure sampling device 60 that incorporates the cell culture plate configuration of the present disclosure and a sample plate. The cell fluid exposure sampling device 60 comprises a first reservoir 61 which contains a fluid that is used to provide the fluid to the sampling device for circulation therein. The second reservoir 75 can be joined to a pump 66a—such as a peristaltic pump—via connectors 65. Between the connectors 65 and the pump 66a, inlet valves 68a—such as electro-valves—can be used to select which reservoir to use. Between the pump 66a and the cell culture plate 62, outlet valves 68b can be included to control the flow of fluid from the pump 66a to the cell culture plate 62. This configuration allows the flow and amount of fluid delivered to the cell culture plate 62 to be precisely controlled. Fluid is circulated through the cell culture plate 62 as described herein. To deliver samples of fluid from the cell culture plate 62 to the sample plate 63, a second channel 64 can be connected or coupled to the first channel 23 in the cell culture plate. A second pump 66b can be used to pump fluid from the cell culture plate 62 to the sample plate 63. Fluid can be conveyed to the sample plate 63 using a pipettor 67—such as a multiple head pipettor. The pipettor 67 can be used to communicate fluid out of the sampling device for further analysis, if required. The pipettor 67 can be an automated pipettor optionally including one or more sensors 72 and optionally one or more electric motors 74 to control the operation thereof. The pipettor 67 can have horizontal motion so that fluid can be conveyed to the sequentially arranged wells in the sample plate 63. Connectors 77 are shown. A waste disposal 78 is also shown. In certain embodiments, the flow rate can be the same for all channels. The different pumps that are used can each have their own pumping parameters. FIG. 10 illustrates a further non-limiting example of a sampling device that can incorporate a cell culture plate and a sample plate and is now described in more detail. In this example, three pumps are shown. Pump 1 is used for refiling the reservoir. Pump 2 is used for circulating fluid through the plate. Pump 3 is used for sampling.

The cell culture plate 62 and the sample plate 63 can have the same number of rows of wells or the sample plate 63 can have a smaller or larger number of rows of wells. A sample is taken from the row of all fluid containing wells of the cell culture plate 62 and delivered into one or more wells of the sample plate 63. Multiple aliquots of the same sample can be dispensed into multiple wells of the sample plate 63 which are suitably all in the same row. Or multiple samples can be taken from the row of fluid containing wells of the cell culture plate 62 at different times points or after exposure to different agents and delivered to the sample plate 63. Typically, the sample taken from the row of fluid containing wells of the cell culture plate 62 will be delivered into the corresponding row of the sample plate 63 so it possible to keep track of the samples from the cell culture plate 62 in the sample plate 63. By way of example, a sample taken from the row of fluid containing wells of the cell culture plate 62 in row 1 will be delivered into one or more wells of the sample plate 63 in row 1. By way of further example, a sample taken from the row of fluid containing wells of the cell culture plate 62 in row 2 will be delivered into one or more wells of the sample plate 63 in row 2, and so on.

The sample collection parameters can be defined in a user interface before starting the experiments, as required The device can be used for various applications as described herein. For example, the device can be used to study the effects of one or more agents during real time exposure. By way of further example, the device can be used to study the kinetics of exposure of one or more agents during real time exposure.

In one aspect, there is provided a method—such as a completely or partially automated method—for sampling cell culture medium exposed to one or more agents comprising the steps of: (a) providing the cell fluid exposure sampling device described herein; (b) contacting at least one of the wells with cell culture medium comprising cells; (c) circulating the cell culture medium through the wells of the cell culture plate; (d) exposing the wells of the cell culture plate to at least one agent; and (e) sampling the cell culture medium from the cell culture plate, optionally wherein the cell culture medium is sampled in real time during exposure to the agent. In step (d), the wells of the multi-well plate can be exposed to at least one agent at multiple time points. The volume of the cell culture medium sampled in step (e) can be between about 50 to about 200 µl. The method can comprise the further step (f) of determining the effect of the agent(s) on the sampled cells.

The use of the cell fluid exposure sampling device for sampling cells from one or more wells of the cell culture plate is also disclosed.

The use of the cell fluid exposure sampling device for sampling cell culture medium exposed to one or more agents from one or more wells of the cell culture plate and screening the cells in the cell culture medium to determine the effect of the one or more agents on the cells is also disclosed.

Screening

The cell culture plate or the sampling device can be used in sampling or screening, optionally, in real-time. The effect of one or more agents on cells contained in the cell culture plate or the device can be determined, optionally, in real time. The cell culture plate and/or the sampling device can be used in, for example, agent/drug discovery, agent/drug characterization, efficacy testing, and toxicity testing and the like. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug/agent interaction assessment, dose assessment, adsorption assessment, disposition assessment, metabolism assessment, elimination studies and the like. Specific cells types may be employed for specific tests (for example, hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity).

In one aspect, there is described an in vitro method for assessing the response of a cell or tissue to an agent, the method comprising: (i) contacting a cell or tissue contained in the cell culture plate or the sampling device described herein with at least one agent; and (ii) measuring one or more responses after contact with the at least one agent; wherein a difference in the one or more responses before and after contact with the at least one agent is indicative that the agent modulates the response of the cell or tissue.

In a further aspect, there is described an in vitro method for assessing the response of two or more cells, tissues or organs to an agent, the method comprising: (i) contacting at least one of the cells, tissues or organs described herein with at least one agent; and (ii) measuring one or more responses in the one or more cells, tissues or organs after contact with the at least one agent; wherein a difference in the one or more responses in the one or more cells before and after contact with the at least one agent is indicative that the agent modulates the response of the at least one cell, tissue or organ.

Suitably, the effect or penetration of at least one agent into the cell or tissue is measured or determined. Suitably, the bio-activation of the at least one agent in the cell or tissue is measured or determined. Suitably, the metabolism of at least one agent by the cell or tissue is measured or determined. These steps can be carried out simultaneously or subsequently to each other.

The effect of one or more agents on the penetration of an agent—such as an aerosol—into the one or more cells, tissues or organs and its further bio-activation or metabolism by another cell or tissue can be determined using the methods described herein.

An agent can be added to one or more wells of the cell culture plate described herein and/or it can be added to the channel of the cell culture plate and its effect on the cultured cell or tissue can be monitored or determined. The agent can also be added to the reservoir(s), as required. Examples of the effects that can be measured include consumption of oxygen, production of carbon dioxide, cell viability, expression of a protein, the activity of an enzyme, penetration, permeability barrier function, surfactant production, response to cytokines, transporter function, cytochrome P450 expression, albumin secretion and the like.

One or more wells of the cell culture plate can be exposed to an aerosol and its effect on the cultured cell or tissue can be monitored or determined. Examples of the effects that can be measured include consumption of oxygen, production of carbon dioxide, cell viability, expression of a protein, the activity of an enzyme, penetration, permeability barrier function, surfactant production, response to cytokines, transporter function, cytochrome P450 expression, albumin secretion and the like.

A plurality of assays may be run in parallel with different concentrations of the agent to obtain a differential response to the various concentrations. As known in the art, the process of determining the effective concentration of an agent typically uses a range of concentrations resulting from 1:10, or other log scale, dilutions. The concentrations may be further refined with a second series of dilutions, if necessary. Typically, one of these concentrations serves as a negative control.

Agent

An agent may be any compound of interest and includes small organic compounds, polypeptides, peptides, higher molecular weight carbohydrates, polynucleotides, fatty acids and lipids, nanoparticles aerosol or one or more components of an aerosol and the like, a drug, a toxin, a pathogen, an antigen, an antibody, and a small molecule and the like. Agents may be screened individually or in sets or combinatorial libraries of compounds. Agents can be obtained from a wide variety of sources including libraries of synthetic or natural compounds. Libraries of natural compounds in the form of bacterial, fungal, plant and animal extracts can be used. Natural or synthetically produced libraries and compounds that are modified through conventional chemical, physical and biochemical means may be used to produce combinatorial libraries. Known pharmacological agents may be subjected to directed or random chemical modifications, such as acylation, alkylation, esterification, acidification to produce structural analogues for screening. When screening using a combinatorial library, a large library of chemically similar or diverse agents can be screened. In combinatorial screening, the number of hits discovered is proportional to the number of agents tested. The large numbers of compounds, which may reach thousands of compounds tested per day, can be screened, in which laboratory automation and robotics may be applied. Many examples of methods for the synthesis of molecular libraries can be found in the art. A small organic compound includes a compound of molecular weight less than about 5000, usually less than about 2500, usually, less than about 2000, more usually, less than about 1500, suitably about 100 to about 1000. The small organic compounds may be either biological or synthetic organic compounds. The atoms present in the small organic compound are generally in the group comprising carbon, hydrogen, oxygen, and nitrogen and may include halogens, boron, phosphorus, selenium and sulphur if in a pharmaceutically acceptable form. Generally, oxygen, nitrogen, sulphur or phosphorus, if present, are bound to carbon or one or more of each other or to hydrogen to form various functional groups such as, for example, carboxylic acids, alcohols, thiols, carboxamides, carbamates, carboxylic acid esters, amides, ethers, thioethers, thioesters, phosphates, phosphonates, olefins, ketones, amines, aldehydes, and the like. The small organic compounds, as the term is used herein, also include small peptides, small oligonucleotides, small polysaccharides, fatty acids, lipids, and the like having a molecular weight less than about 5000.Examples of pharmaceutical agents are described in The Pharmacological Basis of Therapeutics, Goodman and Gilman, McGraw-Hill, New York, N.Y., (1996), Ninth edition. The agent can be a toxin.

Agents in solution and solid samples that can be dissolved in a suitable solvent can be assayed. Agents in gaseous form can also be assayed by exposing samples to the gas for a period of time. Samples of interest include environmental samples, biological samples, manufacturing samples, libraries of compounds and synthetic and naturally occurring compounds.

Polypeptides that have a molecular weight of at least about 5,000, more usually at least about 10,000 can be screened. The test polypeptides will generally be from about 5,000 to about 5,000,000 or more molecular weight, more usually from about 20,000 to about 1,000,000 molecular weight. A wide variety of polypeptides may be considered such as a family of polypeptides having similar structural features, polypeptides having particular biological functions, polypeptides related to specific microorganisms, particularly disease causing microorganisms. Such polypeptides include cytokines or interleukins, enzymes, protamines, histones, albumins, immunoglobulins, scleropolypeptides, phosphopolypeptides, mucopolypeptides, chromopolypeptides, lipopolypeptides, nucleopolypeptides, glycopolypeptides, T-cell receptors, proteoglycans, somatotropin, prolactin, insulin, pepsin, polypeptides found in human plasma, blood clotting factors, blood typing factors, polypeptide hormones, cancer antigens, tissue specific antigens, peptide hormones, nutritional markers, tissue specific antigens, and synthetic peptides, which may or may not be glycated.

Polynucleotides can be screened. The test polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also contemplated. The higher molecular weight polynucleotides can have from about 20 to about 5,000,000 or more nucleotides.

The agent can be a small hydrophobic molecule—such as hydrophobic molecule with a molecular weight of between 146 g/mol and 207 g/mol or between 146 g/mol and 176 g/mol—or an organic solvent with the proviso that the organic solvent is not a halogenated organic solvent or dimethyl sulfoxide or tetrahydrofuran. In one embodiment, the agent comprises or consists of a tobacco alkaloid. In another embodiment, the agent comprises the structure of Formula 1:

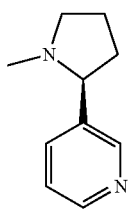

or a pharmaceutically acceptable salt thereof or mixtures thereof;
or, more suitably, the structure of Formula 2:

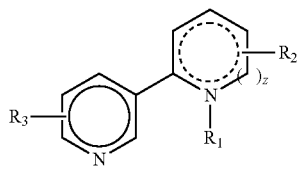

or a pharmaceutically acceptable salt thereof or mixtures thereof;
wherein:
z is 0 or 1;
$R_1$ represents H or $C_1$-$C_7$ alkyl;
$R_2$ represents H, =O, or $C_1$-$C_7$ alkyl;
$R_3$ represents H, halo, or $C_1$-$C_7$ alkyl;
and the dotted line represents either
(a) single bonds;
(b) one carbon/carbon or carbon/nitrogen double bond and the remaining single bonds; or
(c) two conjugated double bonds independently selected from a carbon/nitrogen double bond and a carbon/carbon double bond and the remaining single bonds.
Suitably, the agent of Formula 2 is:

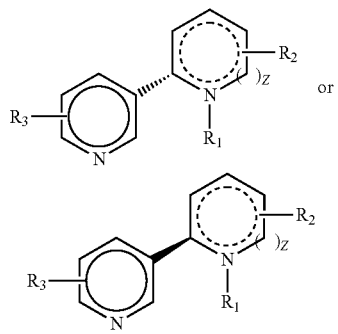

or a pharmaceutically acceptable salt thereof or mixtures thereof.
Suitably, the agent of Formula 2 is:

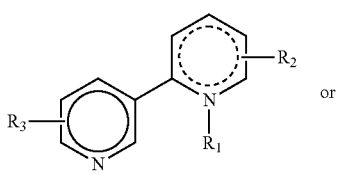

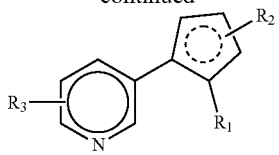

or a pharmaceutically acceptable salt thereof or mixtures thereof.

More suitably, the agent of Formula 1 or Formula 2 is a tobacco alkaloid.

More suitably, the agent of Formula 1 or Formula 2 is nicotine, anabasine, nornicotine, anatabine, cotinine, myosmine or a pharmaceutically acceptable salt thereof or mixtures thereof.

'$C_1$-$C_7$ alkyl' refers to straight chain and branched saturated hydrocarbon groups, generally having from 1 to 7 carbon atoms; more suitably $C_1$-$C_6$ alkyl; more suitably $C_1$-$C_3$ alkyl.

Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like. Suitably, the alkyl group is methyl.

'Halo' refers to F, Cl, Br or I. Suitably, the halo is Cl.

"Pharmaceutically acceptable salt" refers to salts which are within the scope of sound medical judgment suitable for use in contact with the tissues of subjects without undue toxicity, irritation, allergic response, and the like, commensurate with a reasonable benefit-to-risk ratio, and effective for their intended use. These salts include nontoxic acid addition salts (including di-acids) and base salts. If the compound or agent is cationic, or has a functional group which may be cationic (e.g. —$NH_2$ may be —$NH_3^+$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts. For example, if the compound is anionic, or has a functional group which may be anionic (e.g. —COOH may be —COO⁻, or —SO$_2$H may be —SO$_2$), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium (Na⁺) potassium (K⁺), magnesium (Mg²⁺), calcium (Ca²⁺), zinc (Zn²⁺), and aluminum (Al³⁺). Examples of suitable organic cations include, but are not limited to, ammonium ion (i.e. NH$_4^+$) and substituted ammonium ions (e.g. NH$_3$R⁺, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011). Pharmaceutically acceptable salts may be prepared using various methods. For example, one may react a compound or agent with an appropriate acid or base to give the desired salt. One may also react a precursor of the compound or agent with an acid or base to remove an acid- or base-labile protecting group or to open a lactone or lactam group of the precursor. Additionally, one may convert a salt of the compound or agent to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

In another embodiment, the agent is a tobacco-specific nitrosamine (TSNA), which is a chemical formed by the nitrosation of secondary and tertiary amines of tobacco alkaloids including nicotine, nornicotine, anatabine, and anabasine. TSNAs are found in some tobacco and tobacco products. Suitably the TSNA is N-nitrosonicotine (NNN), 4-(methylnitrosamino)-1-(3-pyridyl)-1-butanone (NNK), N-nitrosoanabasine (NAB), N-nitrosoanatabine (NAT), 4-(methylnitrosamino)4-(3-pyridyl)butanal (NNA), 4-(methylnitrosamino)-1-(3-pyridyl)-1-butanol (NNAL), 4-(methylnitrosamino)4-(3-pyridyl)-1-butanol (iso-NNAL), or 4-(methylnitrosamino)-4-(3-pyridyl)-1-butyric acid (iso-NNAC), or a pharmaceutically acceptable salt thereof or mixtures thereof. More suitably, the TSNA is 4-(methyinitrosamino)-1-(3-pyridyl)-1-butanone (NNK) or a pharmaceutically acceptable salt thereof.

In another embodiment, the agent is an organic solvent selected from saturated aliphatic hydrocarbons (e.g., n-pentane, n-hexane, n-heptane, n-octane); aromatic hydrocarbons (e.g., benzene, toluene, xylenes); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents with the proviso that the sulfur-containing solvent is not dimethyl sulfoxide (e.g., carbon disulfide, tetrahydro-thiophene-1,1,-dioxide); and phosphorus-containing solvents (e.g., hexamethylphosphoric triamide).

In one embodiment, the organic solvent is a saturated aliphatic hydrocarbon (e.g., n-pentane, n-hexane, n-heptane, n-octane).

In one embodiment, the organic solvent is an aromatic hydrocarbon (e.g., benzene, toluene, xylenes).

In one embodiment, the organic solvent is an aliphatic alcohol (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol);

In one embodiment, the organic solvent is an ether with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane).

In one embodiment, the organic solvent is a ketone (e.g., acetone, methyl ethyl ketone).

In one embodiment, the organic solvent is an ester (methyl acetate, ethyl acetate).

In one embodiment, the organic solvent is a nitrogen-containing solvent (e.g., formamide, N,N-dimethylformamide, acetonitrile, N-methyl-pyrrolidone, pyridine, quinoline, nitrobenzene).

In one embodiment, the organic solvent is a sulfur-containing solvent with the proviso that the sulfur-containing solvent is not dimethyl sulfoxide (e.g., carbon disulfide, tetrahydro-thiophene-1,1,-dioxide).

In one embodiment, the organic solvent is a phosphorus-containing solvent (e.g., hexamethylphosphoric triamide). In one embodiment, the agent is nicotine or NNK or a combination thereof.

One or more variables that can be measured include quantifiable elements of cells, subcellular material, subcellular components, or cellular products, particularly elements that can be accurately measured in a high throughput assay system or device. An output can be a feature, condition, state or function of any cell, cellular component or cellular product including viability, respiration, metabolism, cell surface determinant, receptor, protein or conformational or posttranslational modification thereof, lipid, carbohydrate, organic or inorganic molecule, DNA, RNA and the like or a portion derived from such a cell component. While the variable(s) can provide a quantitative readout, in some instances a semi-quantitative or qualitative result can be obtained. Readout variables may include a single value, or a mean value, or a median value or a variance thereof, for example.

Various methods can be used to measure the variable(s) to determine the cell, tissue or organ's response to an agent. For measuring the amount of an agent that is present, one method is to label the agent with a detectable moiety, which may be fluorescent, luminescent, radioactive, enzymatically active, and the like. Fluorescent and luminescent moieties are available for labelling a biomolecule, structure, or cell type. Immunofluorescent moieties can be directed to bind not only to specific proteins but also specific conformations, cleavage products, or site modifications like phosphorylation. Individual peptides and proteins can be engineered to auto-fluoresce. Immunoassay techniques—such as immunohistochemistry, radioimmunoassay (RIA), or enzyme linked immunosorbance assay (ELISA) and related non-enzymatic techniques can be used. These techniques utilize specific antibodies as reporter molecules which are particularly useful due to their high degree of specificity for attaching to a single molecular target. Cell-based ELISA or related non-enzymatic or fluorescence-based methods enable measurement of cell surface parameters.

The results of screening assays may be compared to results obtained from reference compounds, concentration curves, controls and the like. The agent can be an aerosol—such as smoke or an aerosol derived from smoke.

Aerosol

Embodiments of the invention can be used for studying the effect of an aerosol on cells, organs or tissues or the penetration of an aerosol into cells, organs or tissues. The aerosol may be derived or generated by an aerosol forming device. Smoking articles and smokable articles are types of aerosol forming devices. Examples of smoking articles or smokable articles include but are not limited to cigarettes, cigarillos, and cigars. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Typically in heated smoking articles, an aerosol is generated by the transfer of heat from a heat source to a physically separate aerosol-forming substrate or material, which may be located within, around or downstream of the heat source. During smoking, volatile compounds are released from the aerosol-forming material by heat transfer from the heat source and entrained in air drawn through the smoking article. As the released compounds cool, they condense to form an aerosol that is inhaled by the user. As used herein, the term 'aerosol forming material' is used to describe a material capable of releasing upon heating volatile compounds, which can form an aerosol. The aerosol forming material may be plant-based. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. The aerosol-forming material may alternatively comprise a non-plant-based-containing material.

The aerosol can be in the form of smoke. As used herein, the term 'smoke' is used to describe a type of aerosol that is produced from combustion, such as from smoking cigarettes, or by combusting an aerosol forming material. Smoke includes various agents, which can be provided as individual compounds for study if required. Examples of such agents include nicotine-free dry particulate matter, carbon monoxide, formaldehyde, acetaldehyde, acetone, acrolein, propionaldehyde, crotonaldehyde, methyl-ethyl ketone, butyraldehyde, benzo[a]pyrene, phenol, m-cresol, o-cresol, p-cresol, catechol, resorcinol, hydroquinone, 1,3-butadiene, isoprene, acrylonitrile, benzene, toluene, pyridine, quinoline, styrene, N'-nitrosonornicotine (NNN), N'-nitrosoanatabine (NAT), N'-nitrosoanabasine (NAB), 4-(methylnitrosamino)-1-(3-pyridyl)-1-butanone (NNK), 1-aminonaphthalene, 2-aminonaphthalene, 3-aminobiphenyl, 4-aminobiphenyl, nitrogen monoxide (NO), nitrous oxide (NOx), cyanhydric acid, ammonia, arsenic, cadmium, chrome, lead, nickel, selenium and mercury.

The cell culture plate described herein can be exposed for various amounts of time to smoke. Smoke can be delivered using a Vitrocell Exposure module (see *Chem Cent J.* (2014) 8(1):62). A defined number of puffs per cigarette and a defined number of puffs per minute of exposure can be used and the number of cigarettes varied to adjust to the exposure times. Reference cigarettes—such as the reference cigarettes 3R4F can be used as the source of the smoke and smoked on the smoking robot in basic conformity with the International Organization for Standardization smoking regimen (ISO 2000).

Computing

Techniques and devices as described herein may be implemented with any suitable hardware, including a programmed computing system. Similarly, the control of a system or device may be controlled by a programmed computing device. The disclosure is operational with numerous other general purpose or special purpose computing system environments or configurations. Examples of well-known computing systems, environments, and/or configurations that may be suitable for use herein can include, but are not limited to, personal computers, server computers, hand-held or laptop devices, multiprocessor systems, microprocessor-based systems, set top boxes, programmable consumer electronics, network PCs, minicomputers, mainframe computers, distributed computing environments or cloud-based computing environments that include any of the above systems or devices, and the like. The computing environment may execute computer-executable instructions, such as program modules. Generally, program modules include routines, programs, objects, components, data structures, etc. that perform particular tasks or implement particular abstract data types. The disclosure may also be practiced in distributed computing environments where tasks are performed by remote processing devices that are linked through a communications network. In a distributed computing environment, program modules may be located in both local and remote computer storage media including memory storage devices.

Components of a computer for use in the present disclosure may include, but are not limited to, a processing unit, a system memory, and a system bus that couples various system components including the system memory to the processing unit. The system bus may be any of several types of bus structures including a memory bus or memory controller, a peripheral bus, and a local bus using any of a variety of bus architectures. By way of example and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer typically includes a variety of computer readable media. Computer readable media can be any available media that can be accessed by the computer and includes both volatile and nonvolatile media, removable and non-removable media.

The computer may operate in a networked environment using logical connections to one or more remote computers, such as a remote computer. The remote computer may be a personal computer, a server, a router, a network PC, a peer device, or some other common network node, and typically includes many or all of the elements described above relative to the computer.

PEEK

As described herein, the inventors have surprisingly found that PEEK has the advantage of not being absorbent towards small hydrophobic molecules—such as hydrophobic molecules with a molecular weight of between 146 g/mol and 207 g/mol or between 146 g/mol and 176 g/mol—or an organic solvent with the proviso that the organic solvent is not a halogenated organic solvent or dimethyl sulfoxide or tetrahydrofuran. PEEK's resistance to absorbance of small hydrophobic molecules or organic solvents is important to prevent or inhibit the trapping of these molecules by this material. Therefore, cell culture plates and other such devices used for culturing cells that are manufactured from a polymer comprising or consisting of PEEK are particularly suitable for the testing of drug or agent effects on the cells or tissues housed within the plate or other such device to avoid or mitigate the risk of the drug or agent concentration (or its metabolites) being altered by the material.

Accordingly, there is disclosed a cell culture device comprising or consisting of PEEK.

Accordingly, there is also disclosed a cell culture device manufactured (exclusively) from PEEK.

There is also disclosed a cell culture plate comprising or consisting of PEEK.

There is also disclosed a cell culture plate manufactured (exclusively) from PEEK.

There is also disclosed a well of a cell culture plate comprising or consisting of PEEK.

There is also disclosed a well of a cell culture plate manufactured (exclusively) from PEEK.

There is also disclosed a multi-well cell culture plate comprising or consisting of PEEK.

There is also disclosed a multi-well cell culture plate manufactured (exclusively) from PEEK.

Suitably, the cell culture device, cell culture plate, well or multi-well cell culture plate comprises one or more small hydrophobic molecules—such as one or more small hydrophobic agents. In one embodiment, the agent comprises or consists of a tobacco alkaloid.

In one embodiment, the agent comprises the structure of Formula 1:

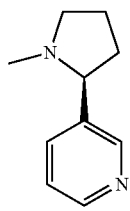

or a pharmaceutically acceptable salt thereof or mixtures thereof;

or, more suitably, the structure of Formula 2:

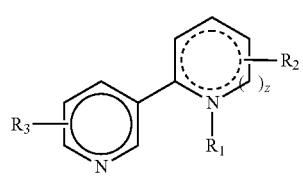

or a pharmaceutically acceptable salt thereof or mixtures thereof;

wherein:
z is 0 or 1;
$R_1$ represents H or $C_1$-$C_7$ alkyl;
$R_2$ represents H, =O, or $C_1$-$C_7$ alkyl;
$R_3$ represents H, halo, or $C_1$-$C_7$ alkyl;
and the dotted line represents either
(a) single bonds;
(b) one carbon/carbon or carbon/nitrogen double bond and the remaining single bonds; or
(c) two conjugated double bonds independently selected from a carbon/nitrogen double bond and a carbon/carbon double bond and the remaining single bonds.

Suitably, the agent of Formula 2 is:

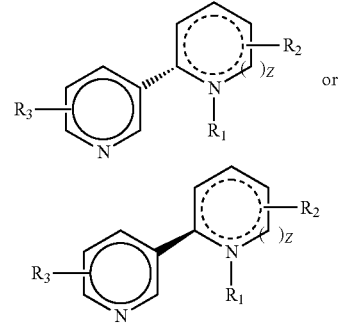

or a pharmaceutically acceptable salt thereof or mixtures thereof.

Suitably, the agent of Formula 2 is:

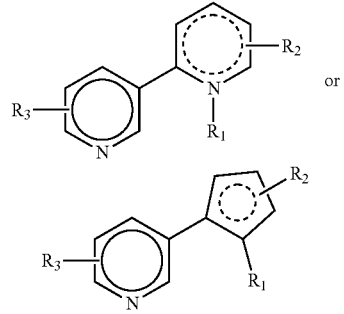

or a pharmaceutically acceptable salt thereof or mixtures thereof.

More suitably, the agent of Formula 1 or Formula 2 is a tobacco alkaloid.

More suitably, the agent of Formula 1 or Formula 2 is nicotine, anabasine, nornicotine, anatabine, cotinine, myosmine or a pharmaceutically acceptable salt thereof or mixtures thereof.

A 'tobacco alkaloid' refers to an alkaloid that is or is derivable from a tobacco plant and can include a synthetic tobacco alkaloid. 'Tobacco plant' refers to a plant belonging to the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N.*

*corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. Suitably, the tobacco plant is *N. tabacum*.

'$C_1$-$C_7$ alkyl' refers to straight chain and branched saturated hydrocarbon groups, generally having from 1 to 7 carbon atoms; more suitably $C_1$-$C_6$ alkyl; more suitably $C_1$-$C_3$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like. Suitably, the alkyl group is methyl.

'Halo' refers to F, Cl, Br or I. Suitably, the halo is Cl.

In another embodiment, the agent is a tobacco-specific nitrosamine (TSNA), which is a chemical formed by the nitrosation of secondary and tertiary amines of tobacco alkaloids including nicotine, nornicotine, anatabine, and anabasine. TSNAs are found in some tobacco and tobacco products. Suitably the TSNA is N-nitrosonicotine (NNN), 4-(methylnitrosamino)-1-(3-pyridyl)-1-butanone (NNK), N-nitrosoanabasine (NAB), N-nitrosoanatabine (NAT), 4-(methylnitrosamino)4-(3-pyridyl)butanal (NNA), 4-(methylnitrosamino)-1-(3-pyridyl)-1-butanol (NNAL), 4-(methylnitrosamino)4-(3-pyridyl)-1-butanol (iso-NNAL), or 4-(methylnitrosamino)-4-(3-pyridyl)-1-butyric acid (iso-NNAC), or a pharmaceutically acceptable salt thereof or mixtures thereof. More suitably, the TSNA is 4-(methylnitrosamino)-1-(3-pyridyl)-1-utanone (NNK) or a pharmaceutically acceptable salt thereof.

Suitably, the organic solvent is selected from saturated aliphatic hydrocarbons (e.g., n-pentane, n-hexane, n-heptane, n-octane); aromatic hydrocarbons (e.g., benzene, toluene, xylenes); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents with the proviso that the sulfur-containing solvent is not dimethyl sulfoxide (e.g., carbon disulfide, tetrahydro-thiophene-1,1,-dioxide); and phosphorus-containing solvents (e.g., hexamethylphosphoric triamide).

In one embodiment, the organic solvent is a saturated aliphatic hydrocarbon (e.g., n-pentane, n-hexane, n-heptane, n-octane).

In one embodiment, the organic solvent is an aromatic hydrocarbon (e.g., benzene, toluene, xylenes).

In one embodiment, the organic solvent is an aliphatic alcohol (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol).

In one embodiment, the organic solvent is an ether with the proviso that the ether is not tetrahydrofuran (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, 1,4-dioxane).

In one embodiment, the organic solvent is a ketone (e.g., acetone, methyl ethyl ketone).

In one embodiment, the organic solvent is an ester (methyl acetate, ethyl acetate).

In one embodiment, the organic solvent is a nitrogen-containing solvent (e.g., formamide, N,N-dimethylformamide, acetonitrile, N-methyl-pyrrolidone, pyridine, quinoline, nitrobenzene).

In one embodiment, the organic solvent is a sulfur-containing solvent with the proviso that the sulfur-containing solvent is not dimethyl sulfoxide (e.g., carbon disulfide tetrahydro-thiophene-1,1,-dioxide).

In one embodiment, the organic solvent is a phosphorus-containing solvent (e.g., hexamethylphosphoric triamide).

In one embodiment, the organic solvent is not petroleum ether.

In one embodiment, the organic solvent is not toluene.

In one embodiment, the organic solvent is not acetone.

In one embodiment, the organic solvent is not ethanol. In one embodiment, the agent is nicotine or NNK or a combination thereof.

There is also disclosed a method for culturing a cell comprising the use of a cell culture device—such as a cell culture plate or a multi-well cell culture plate—comprising or consisting of PEEK.

There is also disclosed a method for culturing a cell comprising the use of a cell culture device—such as a cell culture plate or a multi-well cell culture plate—comprising or consisting of PEEK.

There is also disclosed a method for culturing a cell comprising the use of a cell culture device—such as a cell culture plate or a multi-well cell culture plate—manufactured (exclusively) from PEEK.

There is also disclosed a method for culturing a cell comprising: (i) the contacting a cell with a cell culture device—such as a cell culture plate or a multi-well cell culture plate—comprising or consisting of PEEK; and (ii) culturing the cell.

There is also disclosed a method for culturing a cell comprising: (i) the contacting a cell with a cell culture device—such as a cell culture plate or a multi-well cell culture plate—manufactured (exclusively) from PEEK; and (ii) culturing the cell.

Suitably, the methods discussed above comprise the additional step of contacting the cell in the cell culture device with one or more small hydrophobic molecules or organic solvents as discussed above.

Suitably, the cell culture device can include a cell contained in a cell culture medium and optionally one or more small hydrophobic molecules or organic solvents as discussed above. There is also disclosed a method for determining the effect (for example, the exposure response) of one more agents on a cell comprising: (i) contacting a cell with a cell culture device—such as a cell culture plate or a multi-well cell culture plate—comprising or consisting of PEEK; (ii) exposing the cell to one or more small hydrophobic molecules or organic solvents as discussed above; and (iii) determining the effect of the agent(s) on the cell.

There is also disclosed a method for determining the effect (for example, the exposure response) of one or more agents on a cell comprising: (i) contacting a cell with a cell culture device—such as a cell culture plate or a multi-well cell culture plate—manufactured (exclusively) from PEEK; (ii) exposing the cell to one or more small hydrophobic molecules or organic solvents as discussed above; and (iii) determining the effect of the small hydrophobic molecules or organic solvents as discussed above on the cell.

There is also disclosed a method for reducing or inhibiting the absorbance of one or more small hydrophobic molecules or organic solvents as discussed above into a cell culture device comprising contacting the agent with a cell culture device comprising or consisting of PEEK.

There is also disclosed the use of a cell culture device comprising or consisting of PEEK for reducing or inhibiting the absorbance of one or more small hydrophobic molecules or organic solvents as discussed above into the cell culture device.

The invention is further described in the Example below, which is provided to describe the invention in further detail. This example, which sets forth a preferred mode presently contemplated for carrying out the invention, is intended to illustrate and not to limit the invention.

EXAMPLES

Example 1

Various materials used to manufacture the plate have been investigated. One material used for the plate, PEEK, is a strong plastic polymer that is resistant to wear. PEEK is advantageous in drug testing because it is non-absorbent as opposed to, for example, the commonly used poly(dimethylsiloxane) (PDMS), which is known to retain small hydrophobic molecules. PEEK has surprisingly been found not to retain alkaloids—such as nicotine, or tobacco-specific nitrosamines—such as NNK. Therefore, the plate is suitable for the testing of the effects of these agents on tissues housed within the plate to avoid or mitigate the risk of the agent concentration being altered by the material.

Biocompatibility of the PEEK plate is tested with organotypic lung and liver models.

The lung model is composed of normal human bronchial epithelial (NH BE) cells seeded on a Transwell™ insert and further cultured at the air-liquid interface to ensure differentiation of the cells into goblet and ciliated cells. Using these tissues we can demonstrate that the lung tissues can survive for 4 weeks on the PEEK plate as demonstrated by:

The presence of ciliated and goblet cells in a similar proportion to that observed in control tissues (from the same batch) maintained in 24-well polycarbonate plates for the same duration.

An intact morphology. Histological analysis of tissues maintained in the plate and those maintained in the 24-well plate for 4 weeks confirmed similar morphologies. Epithelial thickness, differentiation state and proportion of goblet, basal and ciliated cells were similar between tissues maintained under these two conditions.

Stable ATP content. ATP is used for several processes in cells and all metabolically active cells contain ATP, which makes ATP content measurements a good indicator for tissue health. Tissues maintained in the plate for 4 weeks had a similar ATP content (ca. 10% less ATP) compared with control tissues.

Active cilia beating. Ciliated cells were not only still present in the same proportion as in control tissues, they were also still actively beating with a frequency similar to the one observed in control tissues.

A higher transepithelial electrical resistance (TEER). TEER measures the integrity of tight junctions in epithelial tissues and is therefore a strong indicator of barrier integrity. Tissues maintained in the PEEK plate had 50% higher TEER values than control tissues.

A retained metabolic capacity. Cytochrome P450 (CYP) inducibility, a hallmark of metabolic capacity, was tested by exposing the tissues to specific CYP enzyme inducers. After 48 hours exposure, CYP 1A1 activity was found to be increased 100 fold demonstrating the retained metabolic inducibility of tissues kept within the plate.

Figure 22:
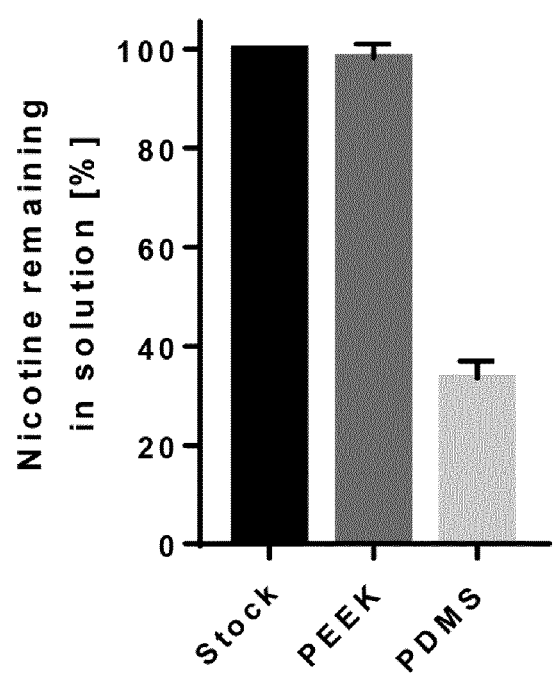
FIG. 22 shows a graph comparing the amount of nicotine remaining in a PEEK plate and a PDMS plate after 8 hours incubation at 4° C.

As a liver model, spheroids composed of HepaRG™ cells are used. The first results obtained with these liver spheroids following 4 weeks of culture within the PEEK plate demonstrate:

A stable secretion of albumin within the circulating medium. Albumin is a key marker of hepatic function. Within the chip albumin was found to be stable for the 4 weeks with a similar concentration has observed with control tissues A retained metabolic capacity. Cytochrome P450 (CYP) inducibility, a hallmark of metabolic capacity, was tested by exposing the tissues to specific CYP enzyme inducers. After 48 hours exposure, CYP 1A1 activity was found to be similar to the inducibility observed in control tissues The absorbance of PEEK towards nicotine and NNK was tested and the found that molecules were not trapped by the material. FIG. 22 shows the results of a graph comparing the amount of nicotine remaining in a PEEK plate and a PDMS plate after 8 hours incubation at 4° C. As can be seen, about 100% of the nicotine remained in the PEEK plate compared to about 35% in the PDMS plate. Thus, materials used for commercially available plates using PDMS will trap small hydrophobic molecules.

Example 2

Figure 21:
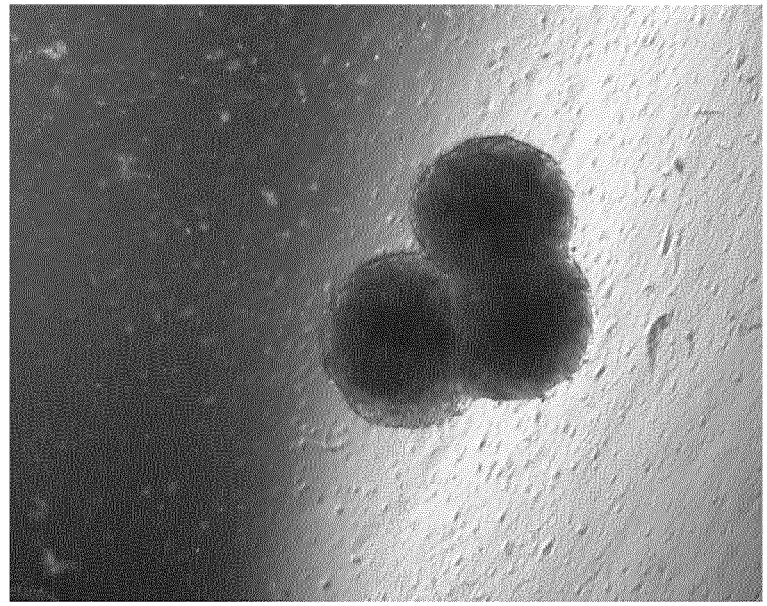
FIG. 21(*a*) shows agglomerated spheroids.
Figure 21:
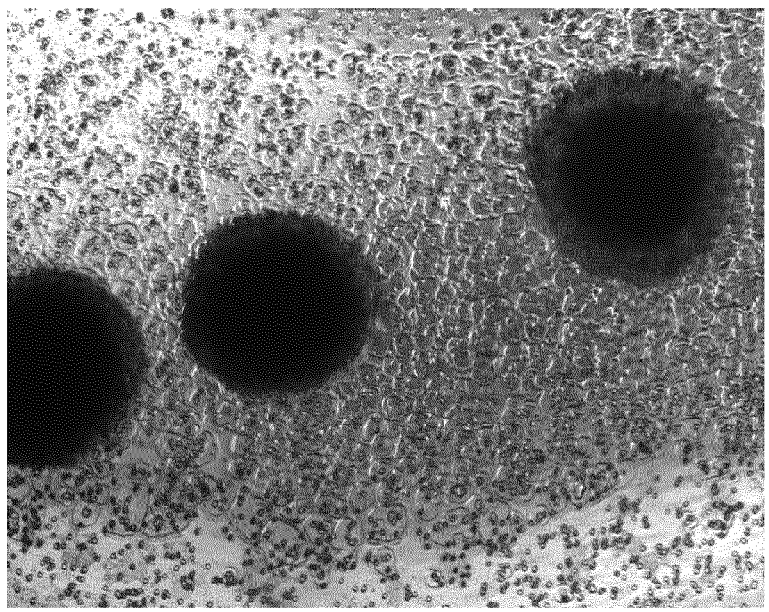

To avoid the agglomeration of spheroids, the well designed for the liver spheroids was adapted to contain concentric grooves on the bottom of the well. The purpose of these grooves is to create a spatial separation between the tissues to prevent them from agglomerating or fusing together. To demonstrate the function of the grooves, 40 spheroids, each composed of about 25,000 cells, were placed either in a well with the grooves or in a well with a flat surface (ie. without grooves). After 5 days, spheroids present in the well with a flat surface were starting to agglomerate together (see FIG. 21A) forming aggregates. This was not observed in the well with the grooves (see FIG. 21B). The tissue shown in FIG. 21A (3 spheroids agglomerated or fused to form a single unit) could not be used for further experiments normally performed on the spheroids—such as measuring the ATP content since the agglomeration or fusion of several spheroids adversely affects the result obtained. The tissue cultured in FIG. 21B did not agglomerate or fuse and was used for further experiments.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in engineering, cellular biology and molecular biology or related fields are intended to be within the scope of the following claims.

The invention claimed is:

1. A cell culture plate comprising:
   at least two sequentially arranged wells; and
   a singular, unitary, and continuous channel having (i) a wall extending from a first end to a second end, (ii) a first end opening at the first end, (iii) a second end opening at the second end, (iv) a first well communication opening in the wall between the first end and the second end, and (v) a second well communication opening in the wall between the first end and the second end,
      wherein the first end of the channel is connected or coupled to a first pump via the first end opening,
      wherein the second end of the channel is connected or coupled to the first pump via the second end opening,
      wherein a first of the at least two sequentially arranged wells is in communication with the channel via the first well communication opening,
      wherein a second of the at least two sequentially arranged wells is in communication with the channel via the second well communication opening, and
      wherein the first pump is operable to circulate fluid between the at least two wells.

2. The cell culture plate according to claim 1, wherein the channel is 3 millimetres or less in diameter.

3. The cell culture plate according to claim 1, wherein the channel is a microfluidic channel.

4. The cell culture plate according to claim 1, wherein the pump is a peristaltic pump, suitably, wherein the peristaltic pump comprises a stepper motor or a brushless motor comprising an encoder.

5. The cell culture plate according to claim 1, wherein the channel is further configured to communicate fluid out of the cell culture plate.

6. The cell culture plate according to claim 5, wherein the channel is connected or coupled to a second pump, wherein said second pump is operable to communicate fluid out of the cell culture plate.

7. A cell fluid exposure sampling device comprising:
   (a) the cell culture plate according to claim 6; and
   (b) a sample plate comprising one or more wells for storing a plurality of samples,
   wherein said second pump is operable to communicate fluid from the cell culture plate towards the sample plate.

8. The cell fluid exposure sampling device according to claim 7, wherein the fluid is communicated to the sample plate using a multiple pipettor.

9. A method for sampling cell culture medium exposed to one or more agents comprising the steps of:
   (a) providing the cell fluid exposure sampling device according to claim 7;
   (b) contacting at least two of the wells with cell culture medium comprising cells;
   (c) circulating the cell culture medium through the wells of the cell culture plate;
   (d) exposing the wells of the cell culture plate to at least one agent; and
   (e) sampling the cell culture medium from the cell culture plate, optionally wherein the cell culture medium is sampled one or more times in real time during exposure to the agent.

10. The cell culture plate according to claim 1, wherein a motor of the first pump and/or a second pump is housed in a waterproof box.

11. The cell culture plate according to claim 1, wherein the cell culture plate is fitted with a lid.

12. The cell culture plate according to claim 11, wherein the lid is not sealed to the cell culture plate to allow air circulation.

13. The cell culture plate according to claim 1, wherein the cell culture plate is housed in an incubator and/or wherein the cell culture plate is manufactured from polyether ether ketone (PEEK).

14. The cell culture plate according to claim 1, wherein the channel is in fluid communication with a plate comprising one or more reservoirs capable of holding a fluid.

15. The cell culture plate according to claim 1, wherein each well has a circular diameter of between about 6 mm and about 16 mm.

16. A cell culture device comprising the cell culture plate according to claim 1 housed inside an incubator.

17. A method for circulating a fluid between two or more sequentially arranged wells comprising:
   (a) providing the cell culture plate according to claim 1;
   (b) contacting the at least two wells with fluid; and
   (c) circulating the fluid through the wells of the cell culture plate.

18. A method for determining the effect of an agent on a cell comprising the steps of:
   (a) providing the cell culture plate according to claim 1;
   (b) contacting the at least two wells of the cell culture plate with cells and cell culture medium;
   (c) circulating the cell culture medium through the wells of the cell culture plate;
   (d) exposing the wells of the cell culture plate to at least one agent;
   (e) removing and testing a sample of cell culture medium from the sequentially arranged wells; and
   (f) determining the effect of the agent on the cells before and after exposure to the at least one agent.

19. The cell culture plate according to claim 1, wherein the cell culture plate is adapted to allow fluid communication between the first well communication opening and the first of the at least two sequentially arranged wells by connecting a hole in the first of the at least two sequentially arranged wells to the first well communication channel, and wherein the cell culture plate is adapted to allow fluid communication between the second well communication opening and the second of the at least two sequentially arranged wells by connecting a hole in the second of the at least two sequentially arranged wells to the second well communication channel.

20. The cell culture plate according to claim 1, further comprising:
   a first well communication channel in communication with the first well communication opening and the first of the at least two sequentially arranged wells; and a second well communication channel in communication with the second well communication opening and the second of the at least two sequentially arranged wells, wherein the channel and the first and second well communication channels are configured in a substantially linear arrangement and are arranged substantially parallel to each other.

21. The cell culture plate according to claim 1, comprising at least three sequentially arranged wells, arranged in series.

22. The cell culture plate according to claim 1, wherein the wells are arranged linearly.

* * * * *